United States Patent
Park et al.

(10) Patent No.: US 11,608,407 B2
(45) Date of Patent: Mar. 21, 2023

(54) CARBON NANOTUBE-FUNCTIONALIZED REVERSE THERMAL GEL AND METHODS OF FORMING AND USING SAME

(71) Applicants: The Regents of the University of Colorado, Denver, CO (US); Universita degli Studi di Trieste, Trieste (IT)

(72) Inventors: Daewon Park, Englewood, CO (US); Brisa Pena Castellanos, Aurora, CO (US); Susanna Bosi, Trieste (IT); Luisa Mestroni, Boulder, CO (US); Maurizio Prato, Trieste (IT)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 256 days.

(21) Appl. No.: 16/649,560

(22) PCT Filed: Sep. 19, 2018

(86) PCT No.: PCT/US2018/051814
§ 371 (c)(1),
(2) Date: Mar. 20, 2020

(87) PCT Pub. No.: WO2019/060456
PCT Pub. Date: Mar. 28, 2019

(65) Prior Publication Data
US 2020/0216601 A1    Jul. 9, 2020

Related U.S. Application Data

(60) Provisional application No. 62/561,098, filed on Sep. 20, 2017.

(51) Int. Cl.
| | | |
|---|---|---|
| *C08G 18/74* | (2006.01) | |
| *C08K 3/04* | (2006.01) | |
| *C01B 32/174* | (2017.01) | |
| *C08J 5/00* | (2006.01) | |
| *B82Y 30/00* | (2011.01) | |
| *B82Y 40/00* | (2011.01) | |
| *C08G 18/38* | (2006.01) | |

(52) U.S. Cl.
CPC ............ *C08G 18/74* (2013.01); *C01B 32/174* (2017.08); *C08J 5/005* (2013.01); *C08K 3/041* (2017.05); *B82Y 30/00* (2013.01); *B82Y 40/00* (2013.01); *C01B 2202/06* (2013.01); *C01B 2202/28* (2013.01); *C08G 18/3829* (2013.01)

(58) Field of Classification Search
CPC ............... C08G 18/74; C08G 18/3829; C08G 18/3831; C08G 18/73; C08G 18/755; C08G 18/7614; C08G 18/7621; C08G 18/765; C08G 18/7671; C08G 18/771; C01B 32/174; C01B 2202/06; C01B 2202/28; C08J 5/005; C08J 2300/14; C08K 3/041; B82Y 30/00; B82Y 40/00; A61L 2400/12; A61L 27/443; A61L 27/52; A61L 2400/06; A61L 2430/20
See application file for complete search history.

(56) References Cited

U.S. PATENT DOCUMENTS

| | | |
|---|---|---|
| 9,284,398 B2 | 3/2016 | Guan et al. |
| 2009/0226704 A1 | 9/2009 | Kauppinen et al. |
| 2010/0247381 A1 | 9/2010 | Yodh et al. |
| 2015/0014577 A1 | 1/2015 | Chowdhury et al. |

OTHER PUBLICATIONS

Peña, et al., Injectable Carbon Nanotube-Functionalized Reverse Thermal Gel Promotes Carbiomyocytes Survival and Maturation, ACS. Appl. Mater. Interfaces 2017; 7: 31645-31656 (Year: 2017).*
Peña et al., "Injectable Carbon Nanotube-Functionalized Reverse Thermal Gel Promotes Cardiomyocytes Survival and Maturation," ACS Appl. Mater. Interfaces, vol. 9, No. 37, Sep. 12, 2017, pp. 31645-31656, XP055585845.
Extended European Search Report dated May 19, 2021 in corresponding European Application No. EP18858150.8.

* cited by examiner

*Primary Examiner* — Daniel C. McCracken
(74) *Attorney, Agent, or Firm* — Snell & Wilmer L.L.P.

(57) ABSTRACT

Polymers suitable for forming carbon nanotube-functionalized reverse thermal gel compositions, compositions including the polymers, and methods of forming and using the polymers and compositions are disclosed. The compositions have reverse thermal gelling properties and transform from a liquid/solution to a gel—e.g., near or below body temperature. The polymers and compositions can be injected into or proximate an area in need of treatment.

6 Claims, 26 Drawing Sheets

100 mg of Commercial MWCNT-COOH in 20 mL of DMF after 30m min of sonication 100 mg of our MWCNT-COOH in 20 mL of DMF after 30m min of sonication

Spontaneous Ca transients

2D Gelatin Control

3D RTG-lysine

3D RTG-CNT

Echocardiography

| Time | Heart Rate (BPM) | | | LVID d (mm) | | | EF% | | |
|---|---|---|---|---|---|---|---|---|---|
| | Saline | RTG | RTG-CNT | Saline | RTG | RTG-CNT | Saline | RTG | RTG-CNT |
| Week 2 | 586 | 503 | 611 | 4.00 | 4.50 | 3.64 | 63.52 | 51.15 | 66.65 |
| Week 4 | 590 | 567 | 609 | 3.77 | 4.11 | 3.86 | 66.89 | 62.81 | 65.63 |
| Week 8 | 533 | 588 | 554 | 4.18 | 3.70 | 3.99 | 65.21 | 68.32 | 68.75 |

FIG.24

Fluorescent labeled miRNA / α-sacomeric-actinin / Nuclei

CARBON NANOTUBE-FUNCTIONALIZED REVERSE THERMAL GEL AND METHODS OF FORMING AND USING SAME

CROSS REFERENCE TO RELATED APPLICATIONS

This application is a U.S. national stage entry under 35 U.S.C. § 371 of International Application No. PCT/US2018/051814 entitled "CARBON NANOTUBE-FUNCTIONALIZED REVERSE THERMAL GEL AND METHODS OF FORMING AND USING SAME," filed Sep. 19, 2018, which claims the benefit of U.S. Provisional Patent Application No. 62/561,098, filed on Sep. 20, 2017, and entitled "CARBON NANOTUBE-FUNCTIONALIZED REVERSE THERMAL GEL AND METHODS OF FORMING AND USING SAME," the disclosures of which are incorporated herein by reference.

STATEMENT REGARDING FEDERALLY SPONSORED RESEARCH OR DEVELOPMENT

This invention was made with government support under grant number HL116905 awarded by the National Institutes of Health. The government has certain rights in the invention.

FIELD OF DISCLOSURE

The present disclosure generally relates to reverse thermal gels, to polymers used to form the reverse thermal gels, to compositions including the polymers, and to methods of forming and using the gels, compositions, and polymers. More particularly, the invention relates to carbon nanotube-functionalized reverse thermal gels and compositions, to polymers used to form the reverse thermal gels and compositions, and to methods of forming and using the polymers, reverse thermal gels and compositions.

BACKGROUND OF THE DISCLOSURE

Heart failure (HF), a leading cause of death worldwide, is a condition in which the heart is unable to efficiently pump blood to the rest of the body, resulting in progressive cardiomyocyte (CMs) dysfunction and can ultimately result in death, absent treatment or transplant. Although a number of studies have detected modest numbers of replicating CMs after cardiac injury, suggesting an attempt at myocardial regeneration, the repair typically occurs through a scarring process, which can lead to tissue fibrosis and loss of function.

Heart transplantation continues to be the gold-standard treatment for end-stage HF. However, complications including the limited availability of donated organs, donor-patient compatibility, immune rejection, and hospitalization costs limit widespread clinical availability.

In light of the limited efficacy and/or availability of current treatments, direct injection of exogenous cells has been used to attempt to repair damaged myocardium. Unfortunately, poor cell survival and retention at the target area limit the therapeutic success of such treatments. In addition, the method of cell delivery and post-transplantation arrhythmias are other major complications for this approach.

As an alternative, various engineered scaffolds have been used to provide a more desirable environment for CMs transplantation. Approaches where CMs are seeded on biomaterial patches have been explored, although engraftment procedures rely on surgical implantations and for patients with severe HF, surgical implantation is rarely an option due to various co-morbidities.

As a minimally invasive alternative, injectable scaffolds have been used to provide a suitable environment for encapsulation of CMs during and after injection into damaged (e.g., infarcted) myocardium. In addition, intra-myocardial biomaterial injection has the potential to reduce wall stress in the infarct area.

While polymeric scaffolds may provide essential mechanical support for CMs and the injured myocardium, the majority of the polymeric materials used for tissue engineering are electrically insulated at biologically-relevant frequencies, and thus do not conduct electrical signals that are critical to cardiac tissue function, such as changes in CMs membrane polarity.

Accordingly, novel techniques for improving CMs growth, survival, function and maturation are desired. Such techniques can be used for the treatment of HF. Further, polymers and compositions suitable for supporting CMs growth, survival, function and maturation are also desired.

SUMMARY OF THE DISCLOSURE

The present disclosure generally relates to compositions with carbon nanotube-functionalized reverse thermal gel properties, to carbon nanotube-functionalized polymers suitable for forming the reverse thermal gels, to methods of forming the compositions and polymers, and to methods of using the compositions and polymers. As set forth in more detail below, the compositions and polymers described herein can be used to support cardiomyocyte (CMs) survival, maturation, and proliferation—e.g., during treatment for heart disease. However, unless otherwise noted, the invention is not limited to such applications.

In accordance with further exemplary embodiments of the disclosure, a carbon nanotube-functionalized reverse thermal gel composition includes (e.g., multi-walled) carbon nanotubes attached to a polymer backbone. The carbon nanotubes can be used to improve electrical, mechanical and/or thermal properties of polymeric materials and gels. Although carbon nanotubes may present poor solubility and potentially an undesirable level of toxicity over a long term, resent investigations have shown that these problems can be solved by chemically introducing functional groups onto the carbon nanotubes. As set forth in more detail below, reverse thermal gels can additionally include molecules bound to the carbon nanotubes and/or to the polymer backbone. Exemplary polymer backbones can include one or more free amine groups for further functionalization of a polymer, allowing polymers and composition described herein to be amenable for a wide variety of bio-conjugations, providing versatility and adaptability for different applications.

In accordance with additional exemplary embodiments of the disclosure, a carbon nanotube-functionalized reverse thermal gel composition is a (e.g., hydrophilic) solution at below a temperature, such as a body temperature or slightly below and becomes a (e.g., hydrophobic) gel at or near (e.g., slightly below) a body temperature (e.g., the composition forms a gel at a temperature of about 25° C. to about 50° C., or about 28° C. to about 50° C., about 30° C. to about 48° C., about 30° C. to about 37° C., or at about 29° C., about 30° C., about 31° C., about 32° C., about 33° C., about 34° C., about 35° C., about 36° C., or about 37° C.). In accordance with various embodiments, the phase transition from solution to gel occurs using only temperature stimuli—i.e., without radiation, use of other solvent, or the like.

Because the carbon nanotube-functionalized reverse thermal gel composition is a liquid below a body temperature, the composition can be relatively easily injected into or proximate an area or tissue to be treated—e.g., myocardium. Further, because the gel transition occurs due to hydrophobic interactions, gel swelling is generally not an issue. The carbon nanotube-functionalized reverse thermal gel composition can then transform from a liquid into a three-dimensional (3D) gel-based matrix (sometimes referred to herein simply as a gel) suitable for, for example, supporting long-term CMs survival, alignment, proliferation, and function. The carbon nanotube-functionalized reverse thermal gel composition can additionally or alternatively provide a minimally-invasive, biocompatible, and non-toxic option for cell (e.g., CMs) transplantation.

As noted above, in accordance with exemplary embodiments of the disclosure, a carbon nanotube-functionalized reverse thermal gel composition includes carbon nanotubes attached to a polymer backbone. The polymer backbone can include, for example a polyurea-polyurethane polymer backbone (e.g., poly(serinol hexamethylene urea) or PSHU). PSHU is also highly biomimetic and biocompatible, since amide ester bonds in the backbone structure provide characteristics similar to those found in natural polymers, such as collagen and gelatin. The polymer backbone can include the general formula:

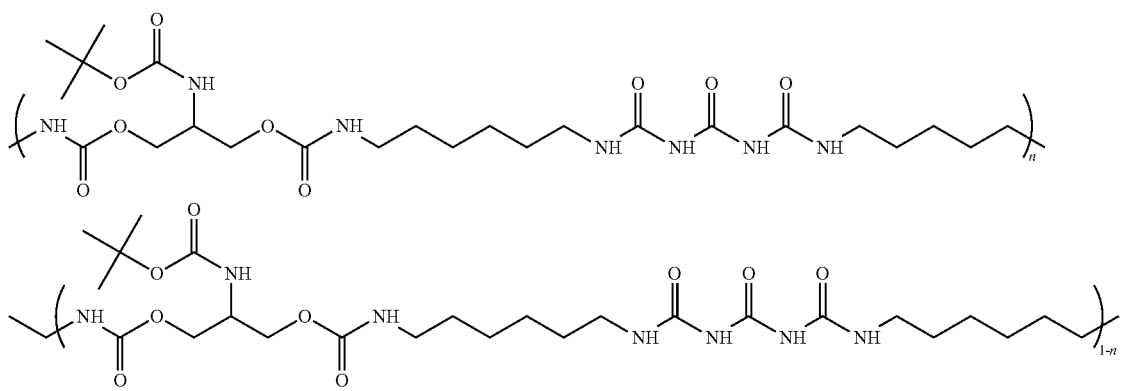

where, for example, n ranges from about 1 to about 18 repeat units.

In accordance with further exemplary embodiments, the polymer backbone can be functionalized with poly(N-isopropylacrylamide) PNIPAAm. An exemplary polymer functionalized with PNIPAAm is illustrated below, where n can be the same as noted above and m ranges from 27 to 890 repeat units.

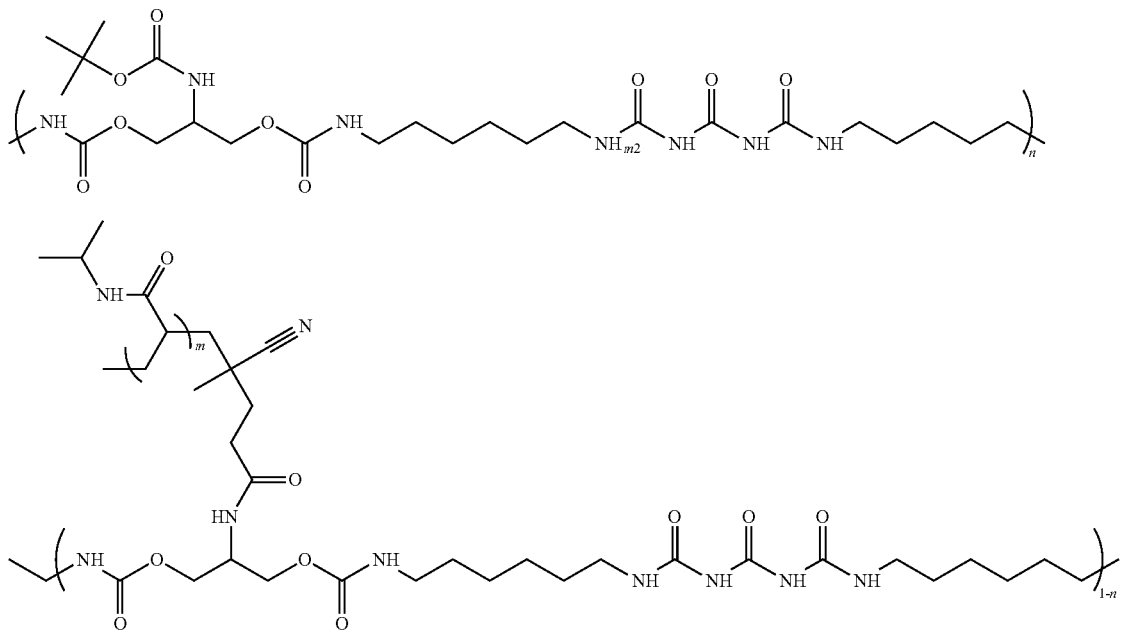

In accordance with further exemplary embodiments, the polymer backbone can be functionalized with poly-L-lysine. An exemplary polymer functionalized with poly-L-lysine is illustrated below, where n, m, can be the same as noted and m2 ranges from 5 to 50 repeat units.

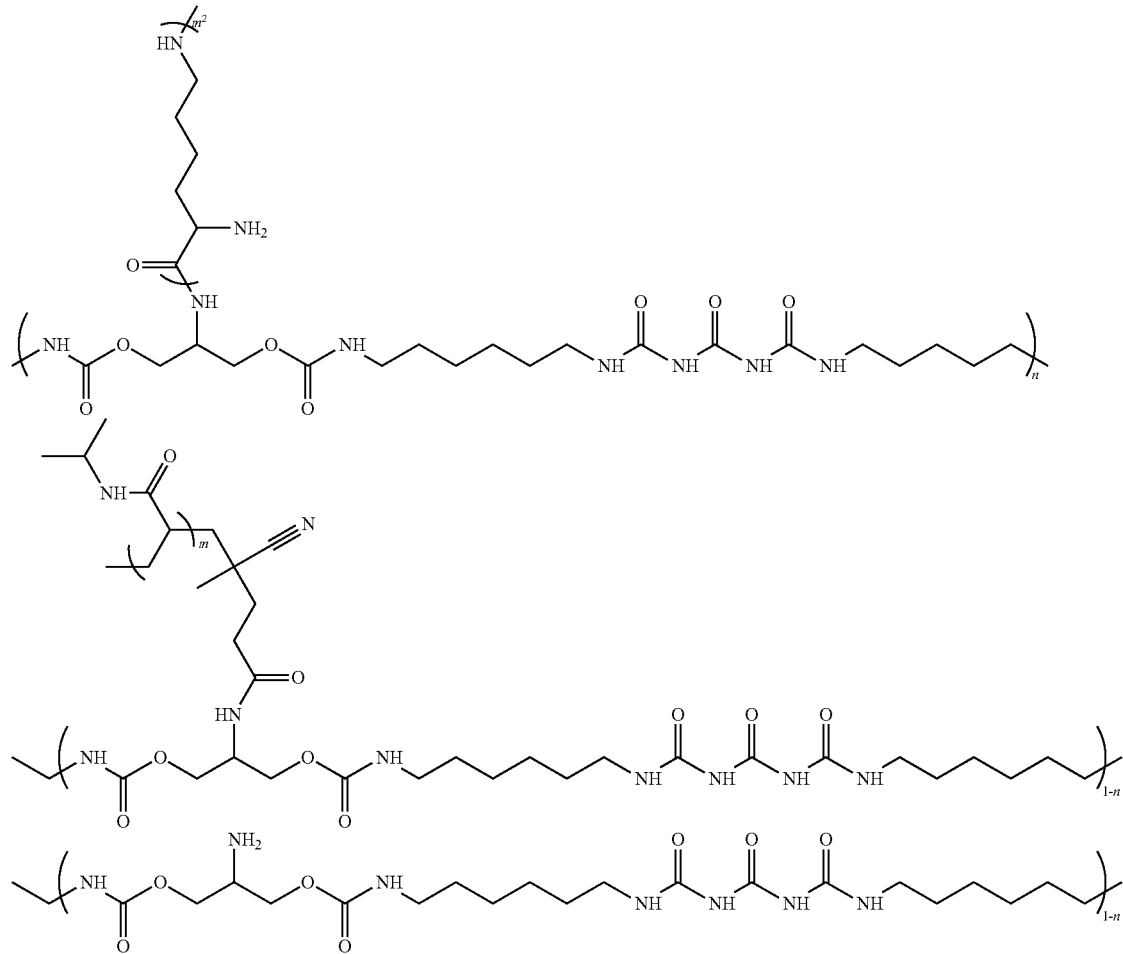

In accordance with further examples, PNIPAAm and carbon nanotubes and optionally the poly-L-lysine are attached to a polymer backbone. An exemplary polymer functionalized with PNIPAAm, carbon nanotubes and (optionally poly-L-lysine) is illustrated below.

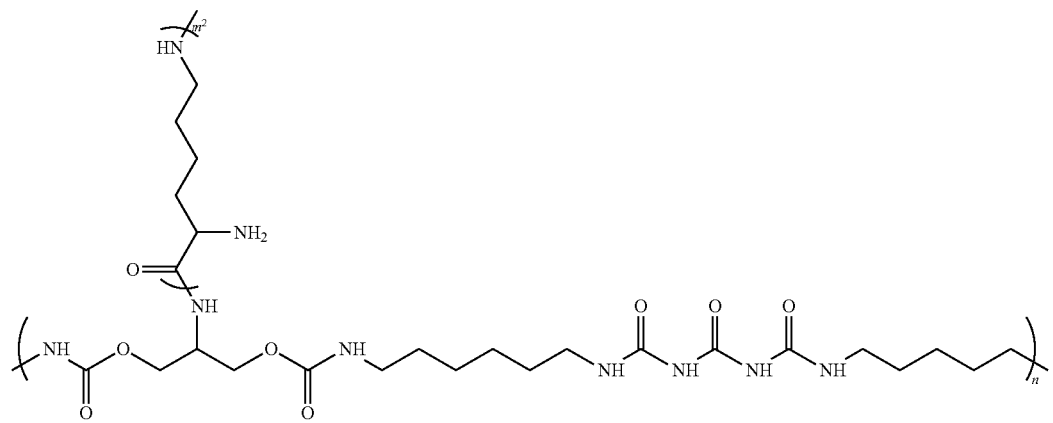

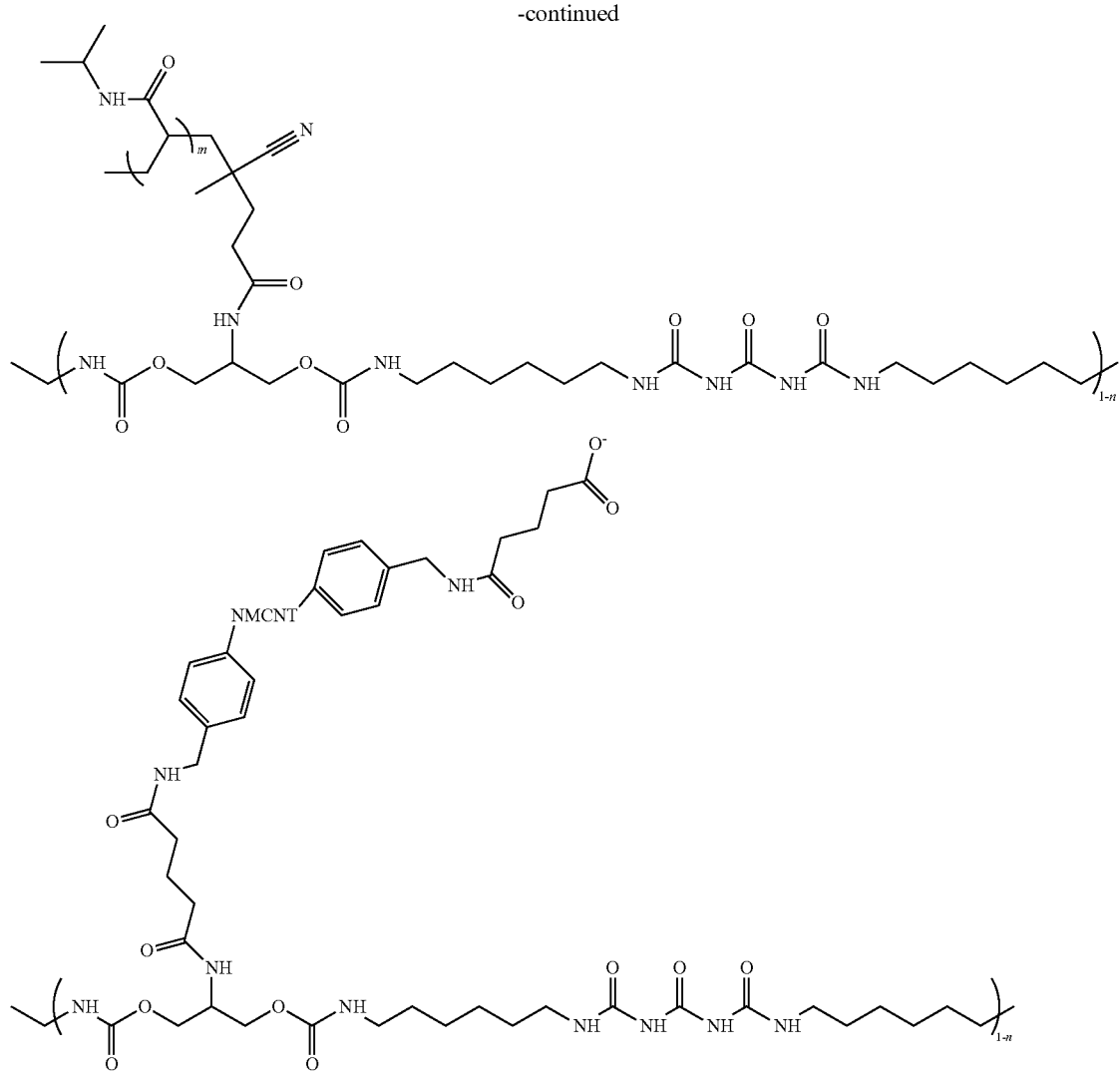
In accordance with further exemplary embodiments of the disclosure, the polymer can include poly-L-lysine conjugated to one or more carbon nanotubes that are conjugated onto the polymer backbone. An exemplary formula for such a polymer is provided below.
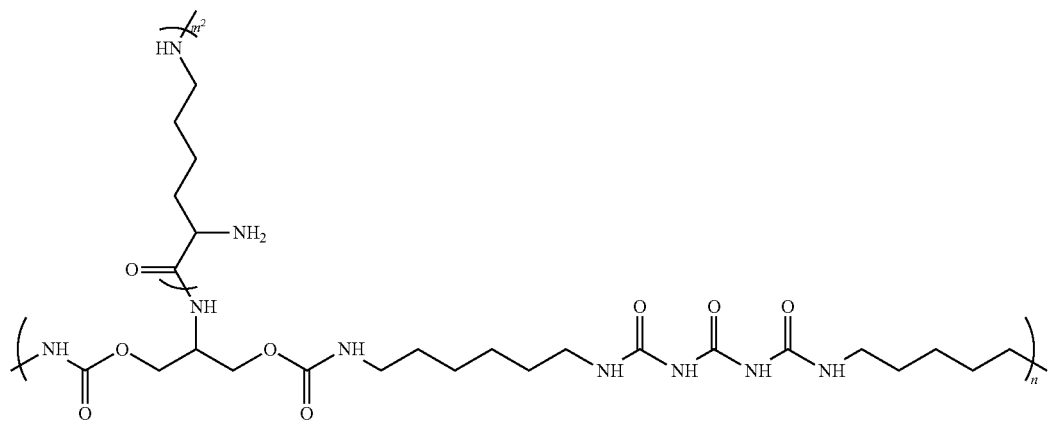

-continued

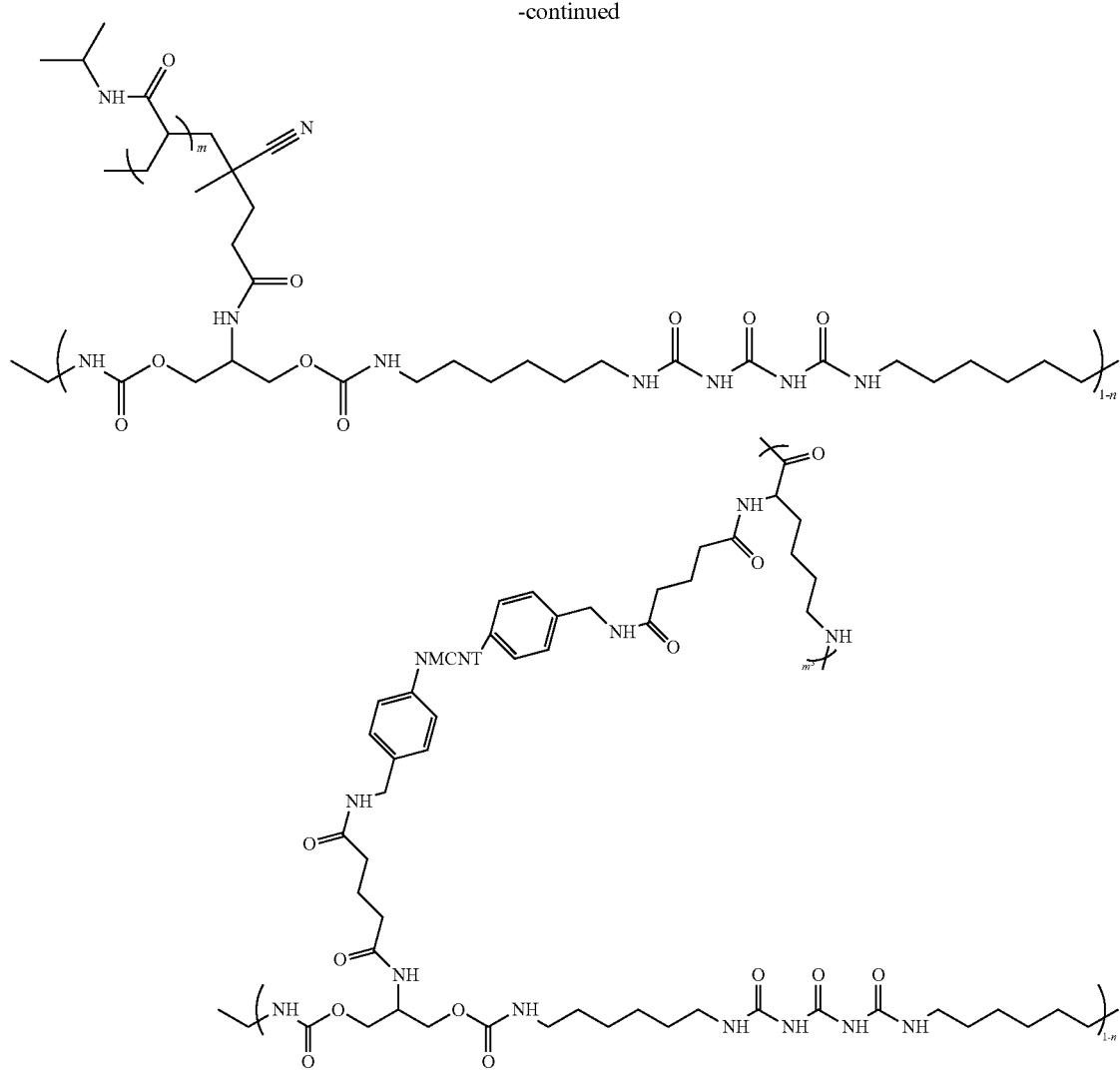

In accordance with further aspects, a carbon nanotube-functionalized reverse thermal gel composition comprises, consists essentially of, or consists of a polymer, such as a polymer described herein, optionally cardiomyocytes, proliferative miRNAs such as, miR-590 and miR-199 and/or other bioactive material, such as the bioactive materials described herein, and optionally a carrier—e.g., comprising a diluent—e.g., water or saline solution. The composition can include, for example, about 1% (w/w) to about 20% (w/w), about 5% (w/w) to about 15% (w/w) or about 8% (w/w) to about 10% (w/w) polymer in solution. Additionally or alternatively, the composition can include, for example, about 0.1% (w/w) to about 1% (w/w), about 2% (w/w) to about 10% (w/w) of bioactive material.

In accordance with yet further exemplary embodiments of the disclosure, a method of forming a carbon nanotube-functionalized reverse thermal gel composition includes the steps of: synthesizing multi-walled carbon nanotubes with COOH groups, synthesizing a reverse thermal gel polymer backbone, conjugating poly-L-lysine onto the polymer backbone, and conjugating at least one of the carbon nanotubes onto the L-lysine. The step of synthesizing a reverse thermal gel polymer backbone can include, for example, synthesizing PSHU (e.g., from urea N—BOC-serinol and a diisocyanate to form PSHU—NH$_2$) and conjugating PNIPAAm-COOH onto the PSHU (PSHU—NH$_2$). Exemplary methods can further include a step of conjugating another poly-L-lysine onto the at least one of the carbon nanotubes.

In accordance with additional exemplary embodiments of the disclosure, a method of synthetizing multi walled carbon nanotubes with COOH groups includes incorporation of amino benzyl groups onto (e.g., multi walled) carbon nanotubes via the diazonium salt arylation reaction route and then conjugating succinic anhydride to incorporate the COOH groups.

In accordance with yet additional exemplary embodiments of the disclosure, a method of using a carbon nanotube-functionalized reverse thermal gel composition includes the steps of providing a carbon nanotube-functionalized reverse thermal gel composition, such as a composition as described herein, and applying (e.g., injecting) the carbon nanotube-functionalized reverse thermal gel composition in or proximate an area to be treated. For example, the composition can be injected into myocardium. The composition can be used for tissue engineering. By way of examples, the composition can be used to support CMs survival, maturation, and proliferation after application/injection. Additionally, or alternatively, the composition can be used as a delivery system for miRNA (e.g., miR-199a and/or miR-590) transfection to induce CMs proliferation and/or for injection of CMs.

BRIEF DESCRIPTION OF THE DRAWING FIGURES

A more complete understanding of exemplary embodiments of the present disclosure may be derived by referring to the detailed description and claims when considered in connection with the following illustrative figures.

Figure 9:
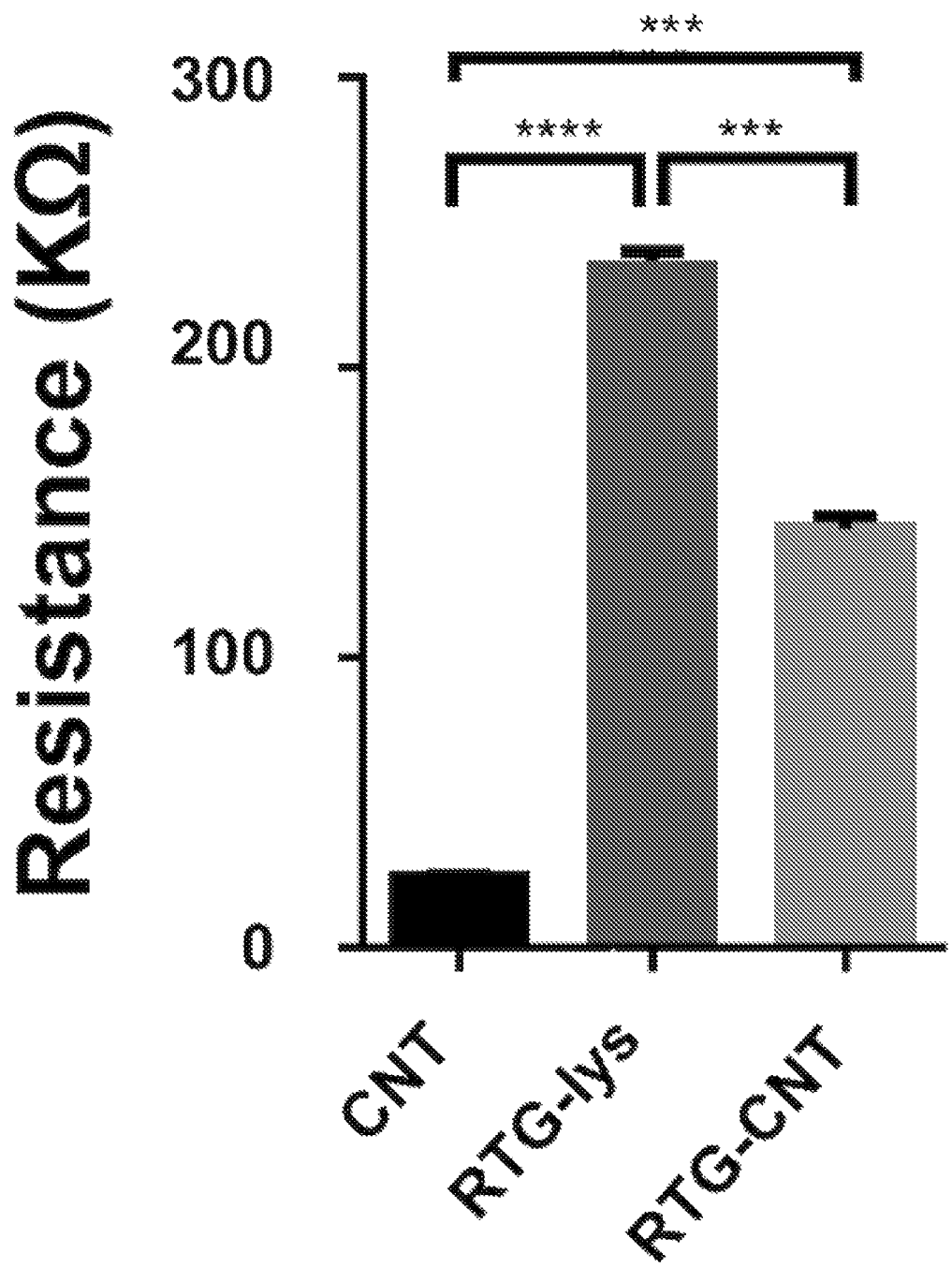

FIG. 9 illustrates resistance measurements: the hybrid CNT-RTG presented a resistance between both the RTG polymer and the CNT-COOH. (ANOVA-Dunn's test) (CNT-COOH "vs" RTG-lysine **p value: <0.0001; n=20; RTG-lysine "vs" RTG-CNT *p value: 0.0002; n=20; RTG-CNT "vs" CNT-COOH ***p value: 0.0002, n=20).

Figure 10:
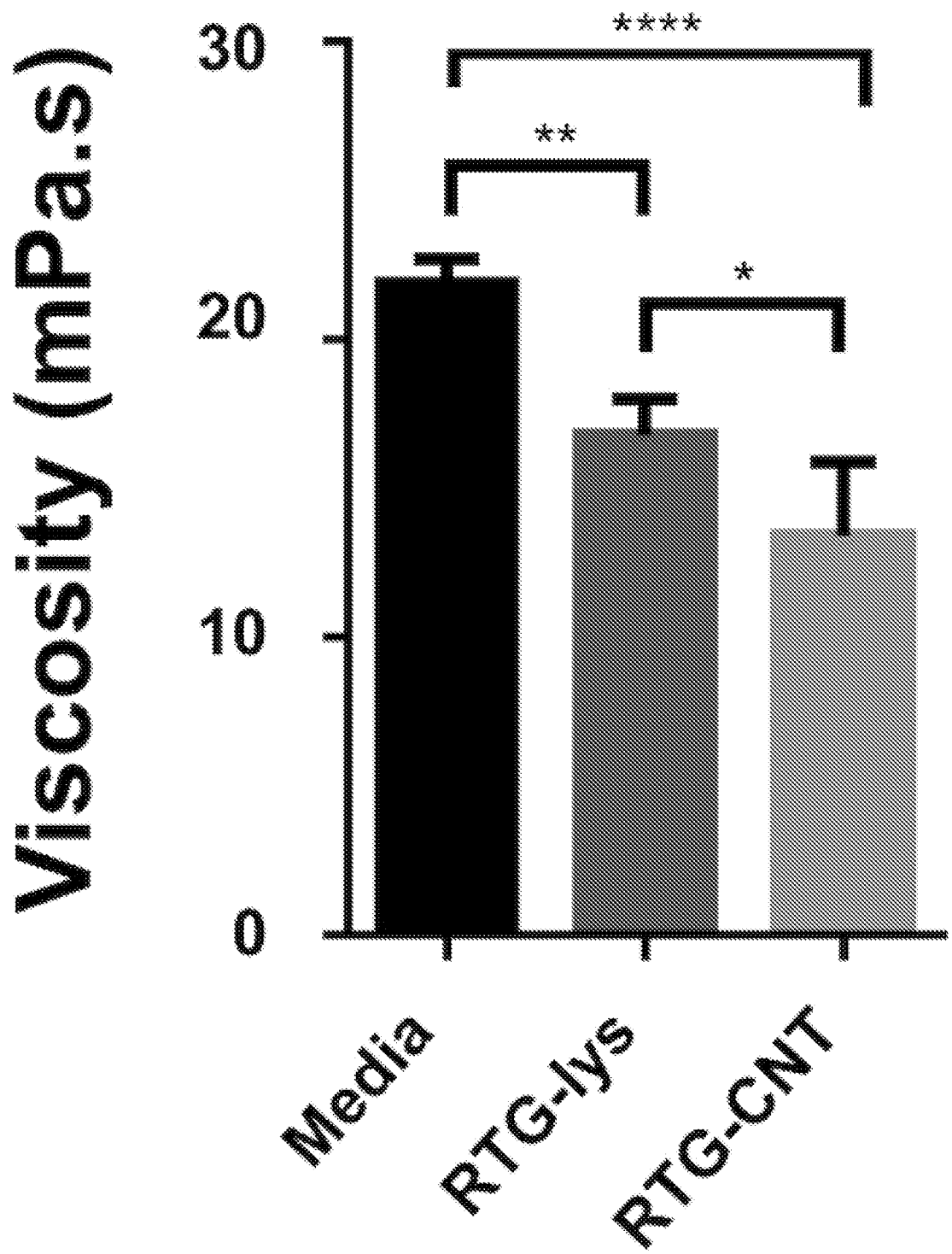

FIG. 10 illustrates RTG and CNT-RTG systems present lower viscosity than media. (ANOVA-Bonferroni's test) (media "vs" RTG-lysine **p value: 0.0013; n=5; RTG-lysine "vs" RTG-CNT *p value: 0.0238; n=5; RTG-CNT "vs" media ****p value: <0.0001, n=5).

Figure 11:
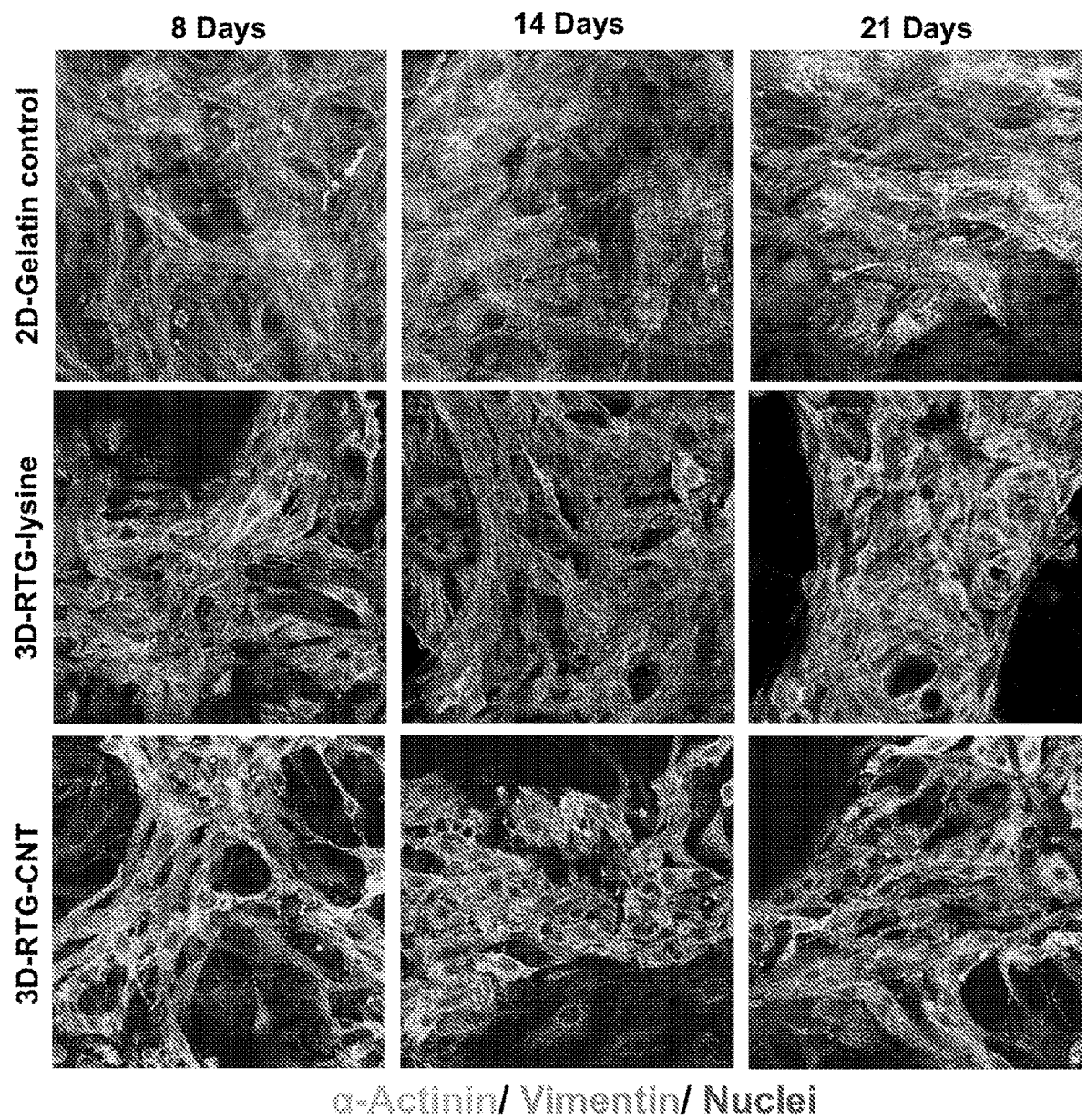

FIG. 11 illustrates fluorescence staining of NRVMs and fibroblasts cultured in different substrates; sarcomeric α-actinin, vimentin and DAPI. Top-row panels: NRVMs cultured on 2D gelatin control. Middle-row panels: NRVMs cultured in 3D RTG-lysine. Bottom-row panels: NRVMs cultured in 3D RTG-CNT.

Figure 12:
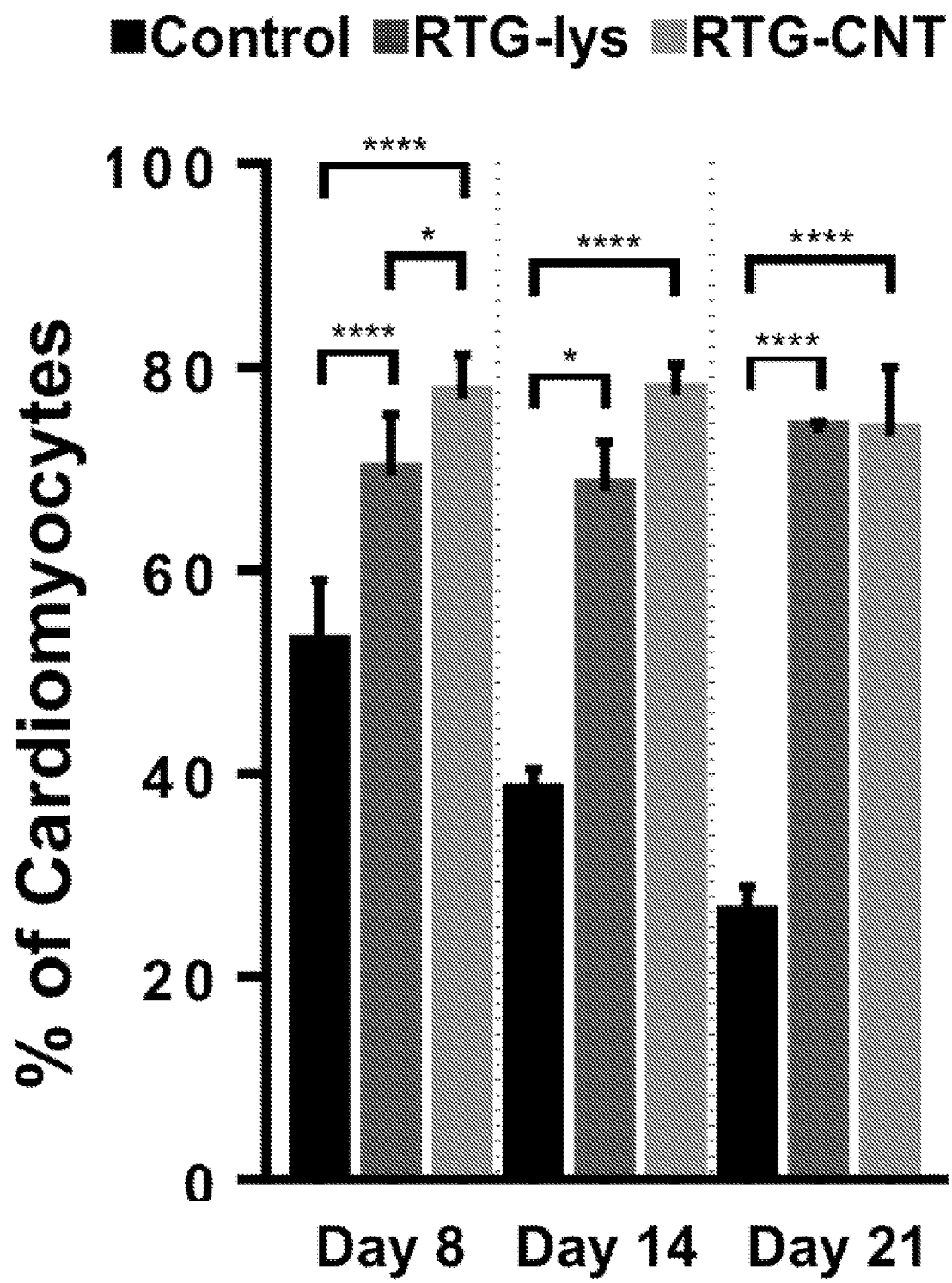

FIG. 12 illustrates quantification of the percentage of NRVMs growing in gelatin-control and the RTG systems.

Figure 13:
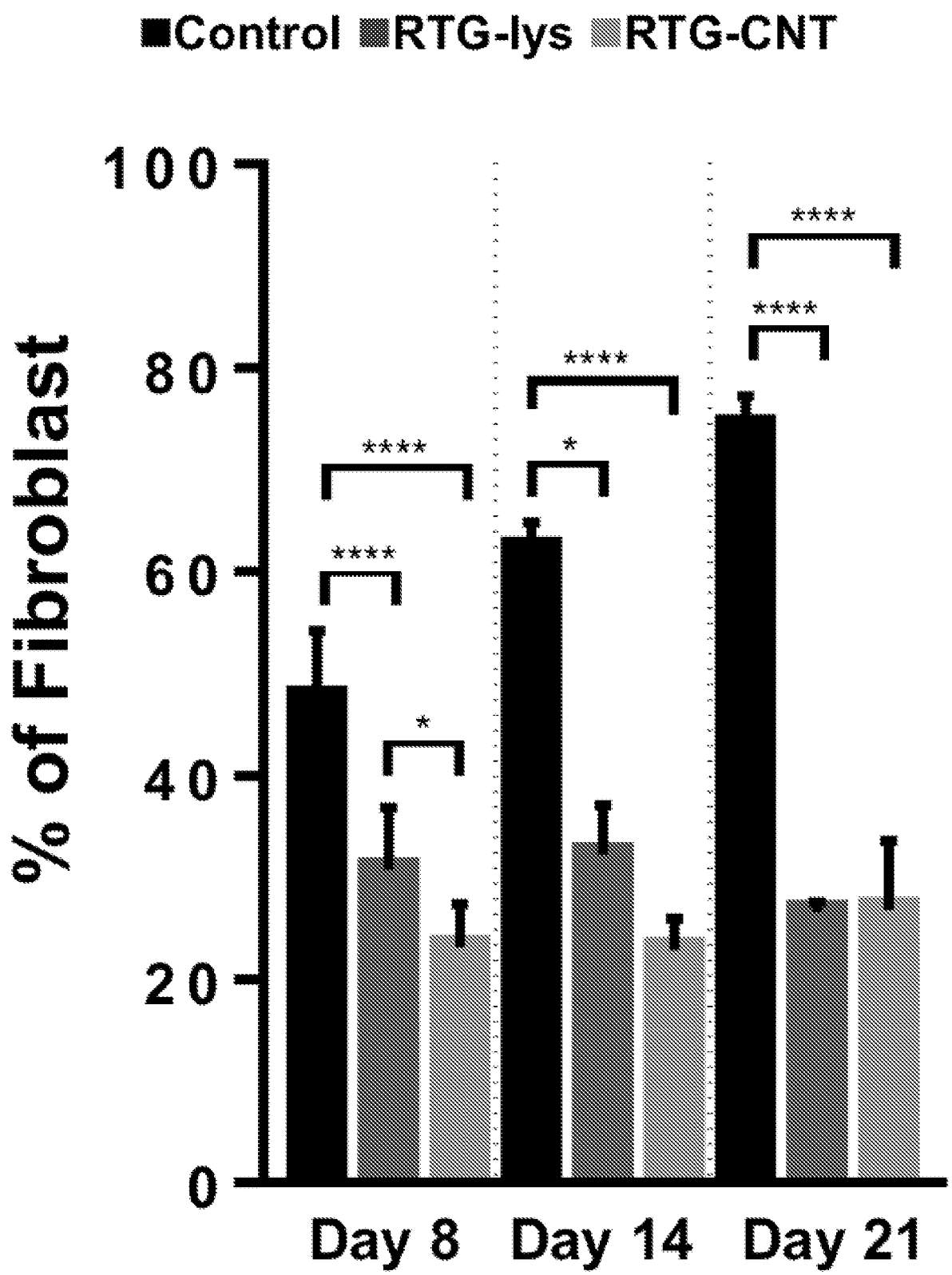

FIG. 13 illustrates quantification of the percentage of fibroblast growing in gelatin-control and the RTG systems.

Figure 14:
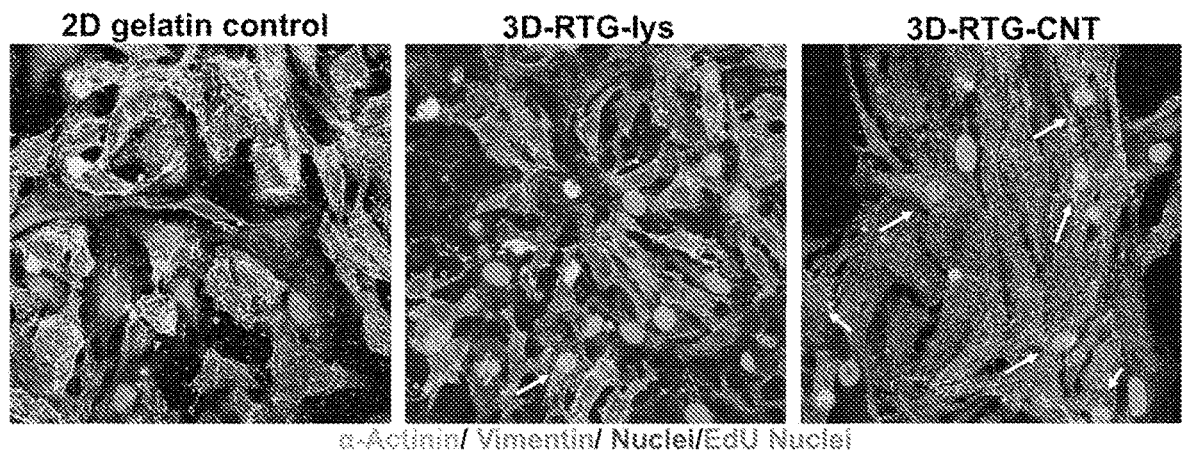

FIG. 14 illustrates proliferation assay of NRVMs and fibroblasts. From left to right: NRVMs and fibroblast cultured on 2D gelatin control, 3D RTG-lysine and 3D RTG-CNT at day 4.

Figure 15:
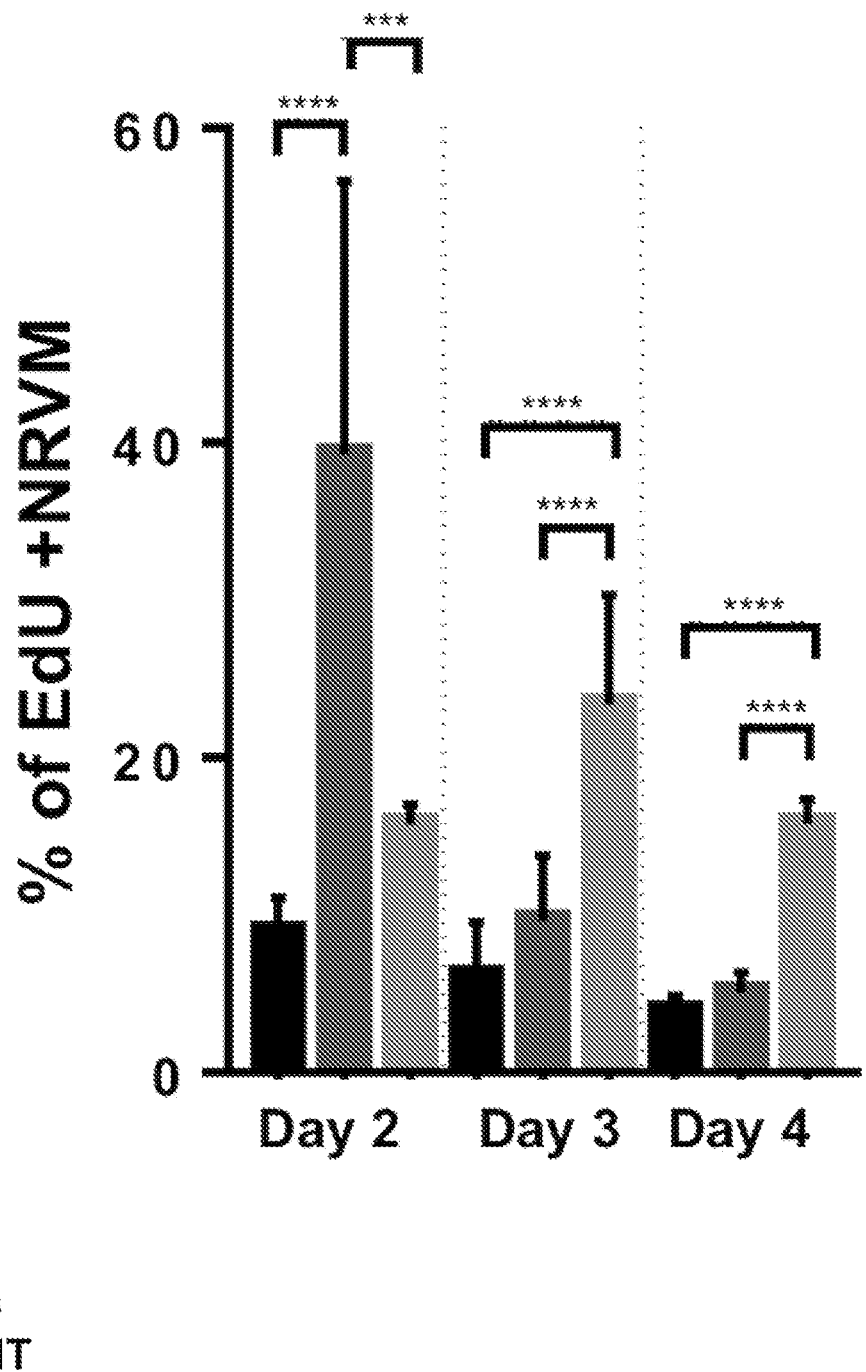

FIG. 15 illustrates significant differences of dividing NRVMs on the RTG-lysine system were observed when compared with the gelatin controls.

Figure 16:
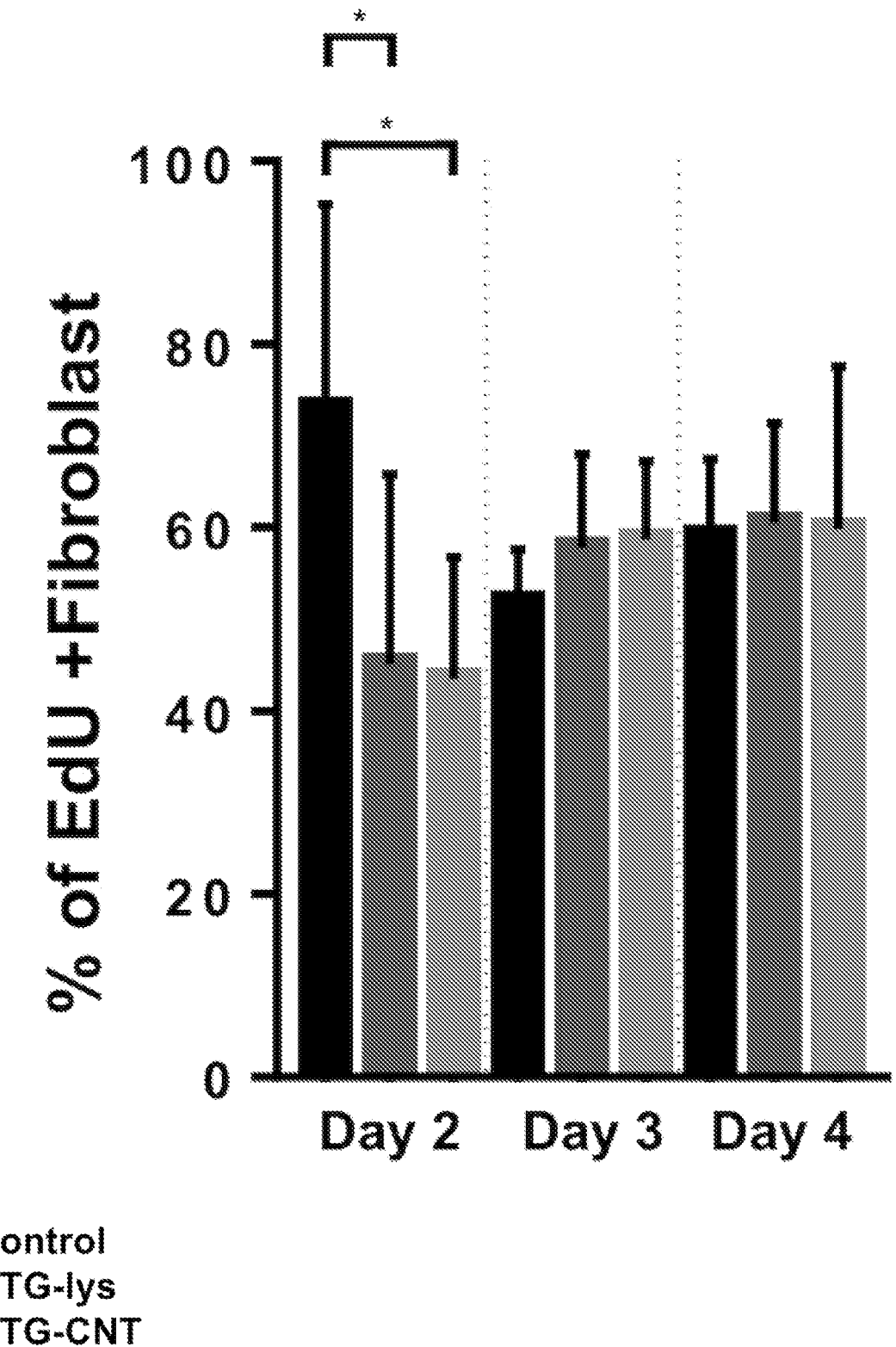

FIG. 16 illustrates significant differences of dividing fibroblast on the RTG-lysine system were observed when compared with the gelatin controls.

Figure 17:
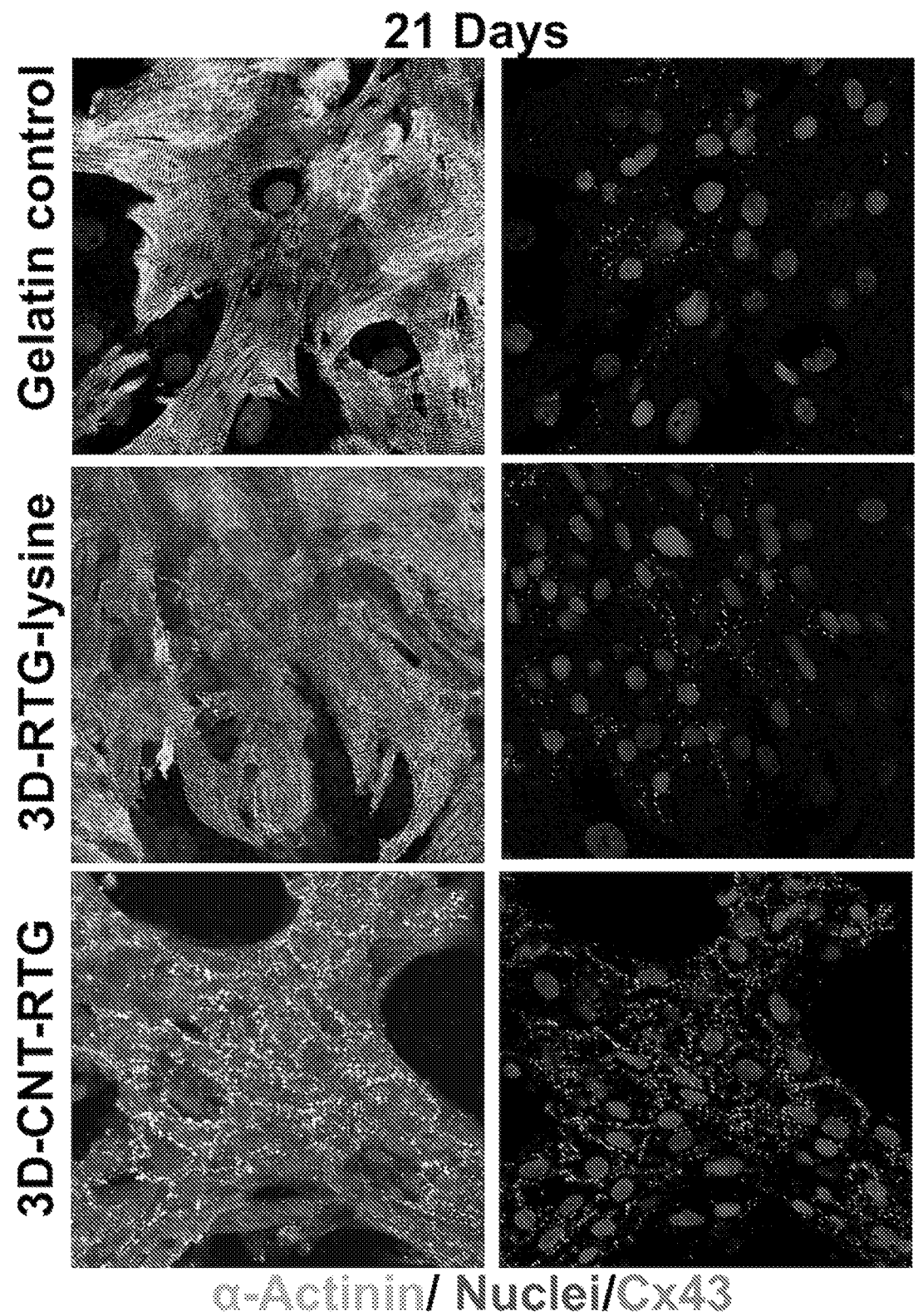

FIG. 17 illustrates intercellular communication of NRVMs growing in different substrates after 21 days of culture.

Figure 18:
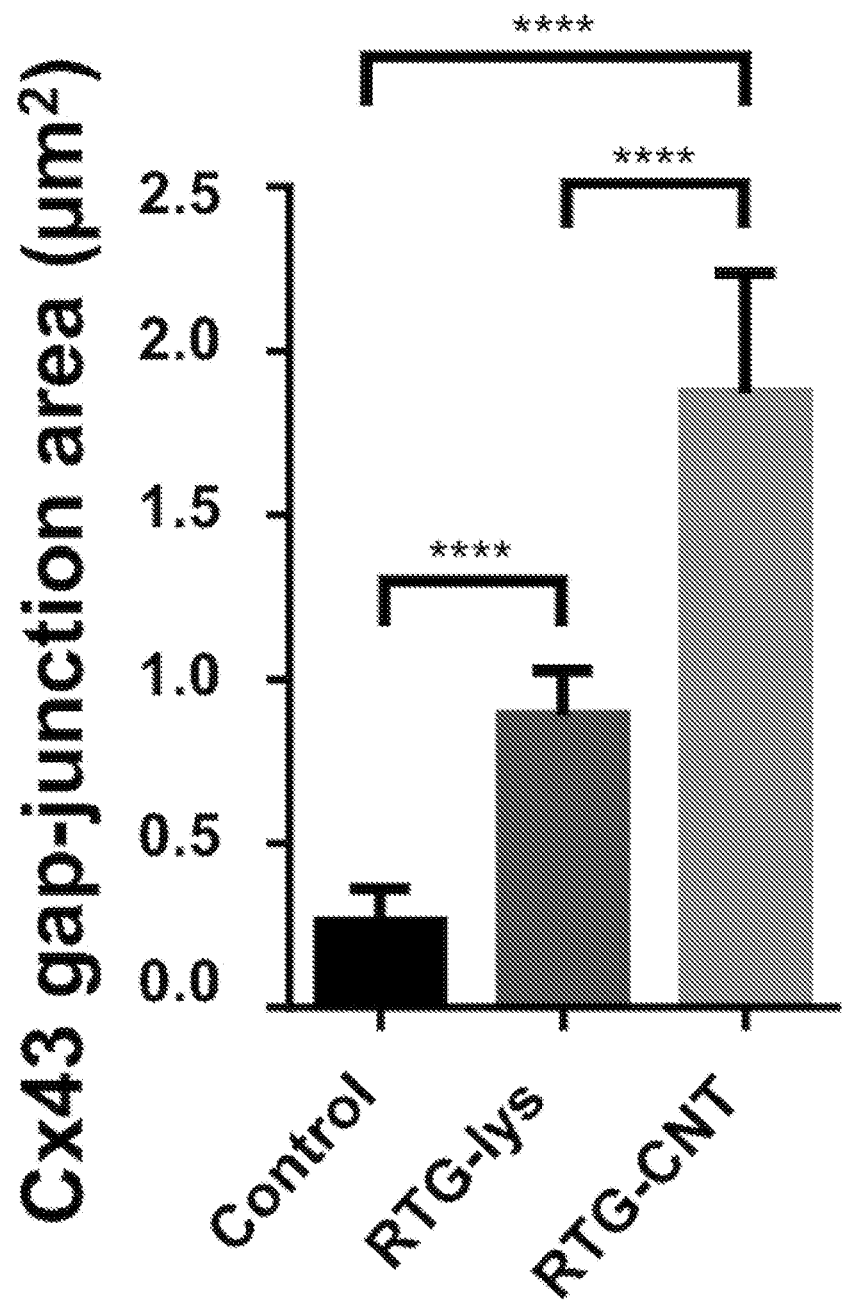

FIG. 18 illustrates quantification of Cx43 gap junction area: significant differences on Cx43 gap-junction were observed between the gelatin control groups and the RTG systems.

Figure 19:
Figure 19:
Figure 19:
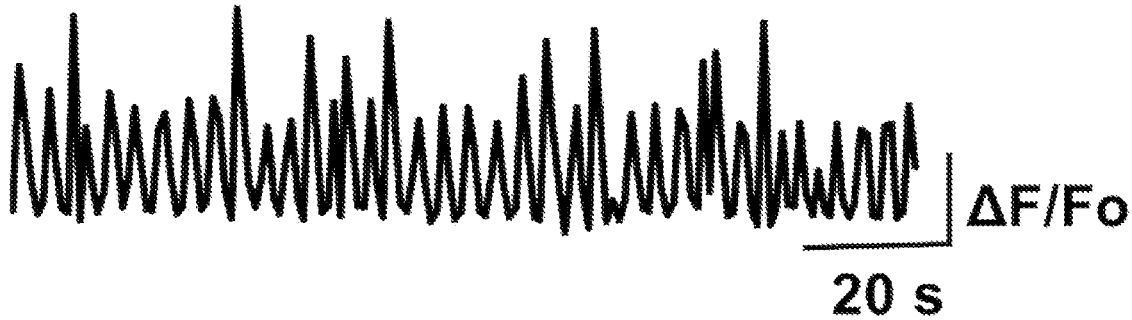

FIG. 19 illustrates spontaneous calcium transients of NRVMs growing on 2D gelatin control and in 3D RTG systems (n=5).

Figure 20:
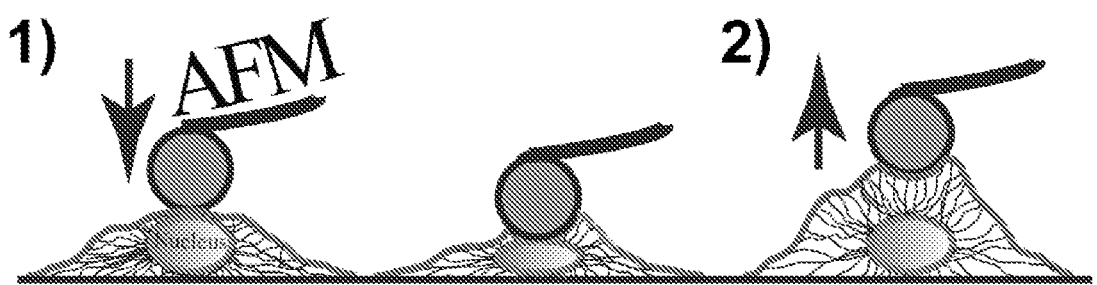

FIG. 20 illustrates a schematic representation of the beating activity of NRVMs measurements by the deflection of the AFM cantilever. From left to right: AFM cantilever gently pushing the nuclear region the CM, the beating activity of CM pushed away the AFM cantilever, providing information about beating height and frequency.

Figure 21:
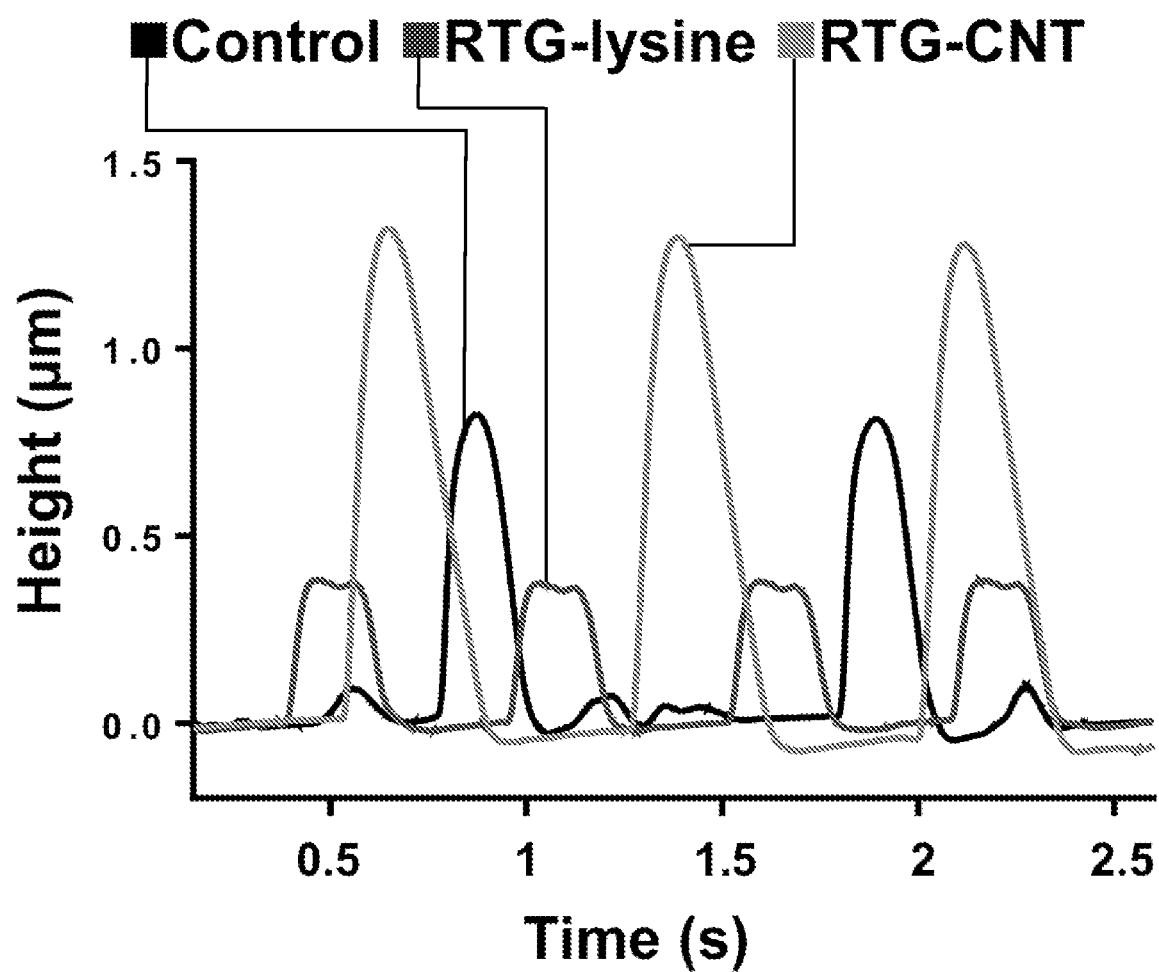

FIG. 21 illustrates NRVMs cultured in the 31) RTG-CNT presented higher contraction while beating suggesting that the CNT-RTG niche supports a stronger cardiomyocyte contraction.

Figure 22:
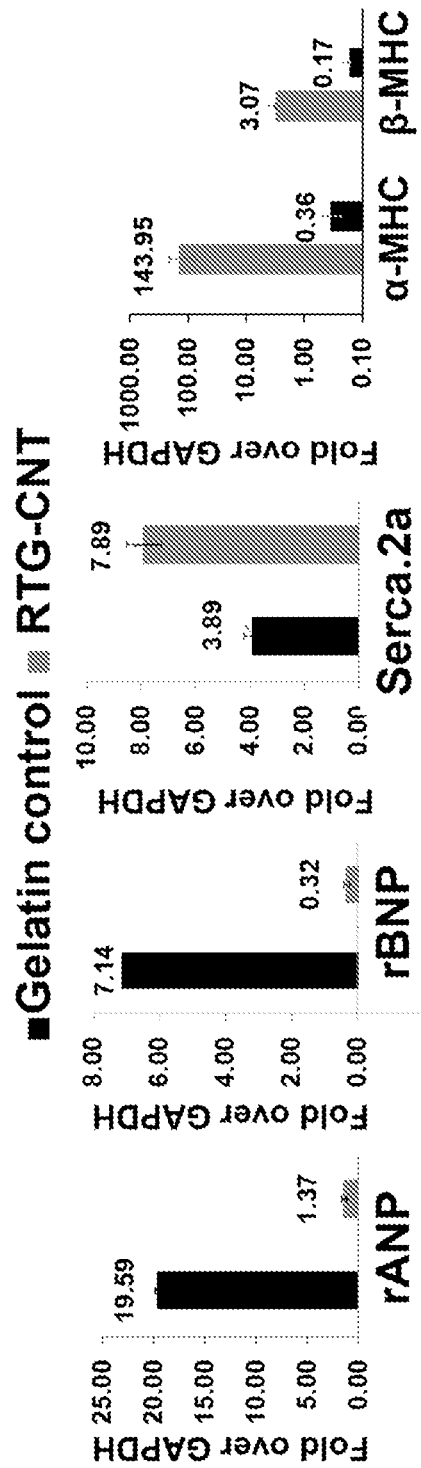

FIG. 22 illustrates the gene expression analysis of NRVM cultured for 21 days in 2D gelatin coated dishes and in the 3D RTG-CNT polymer.

Figure 23:
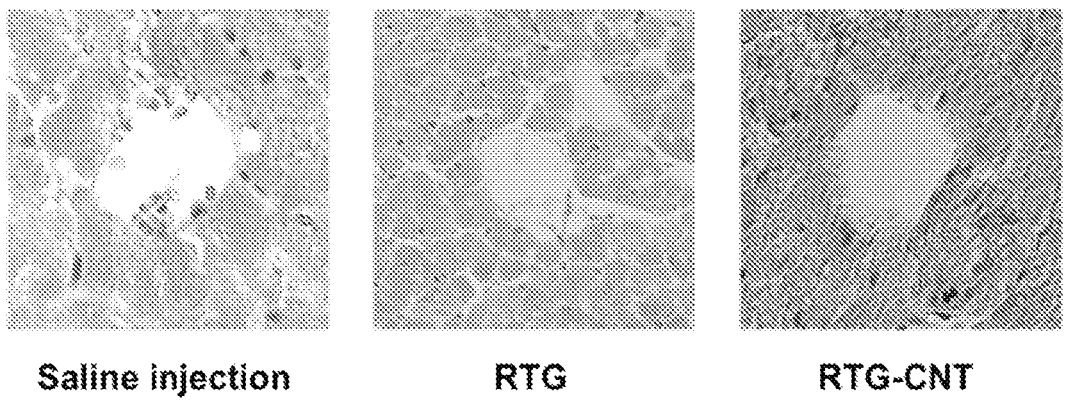

FIG. 23 illustrates the RTG polymers and saline injections in mice heart tissue stained with hematoxylin and eosin.

FIG. 24 illustrates the echocardiographic results after the injections indicating normal heart function after polymers injection. IVS: Interventricular septum; d: diastole; s: systole; LVID: Left ventricular internal diameter; EF %: ejection fraction; FS %: Fraction shortening; LV Vol: left ventricle volume.

Figure 25:
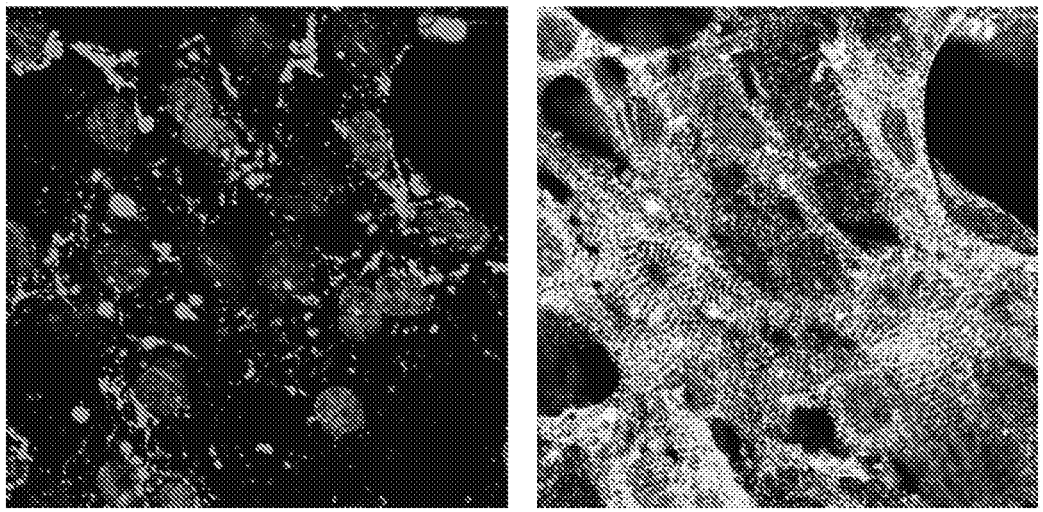

FIG. 25 illustrates the NRVM transfected with a fluorescent-labeled miRNA using the RTG-CNT system as transfection vector.

Figure 26:
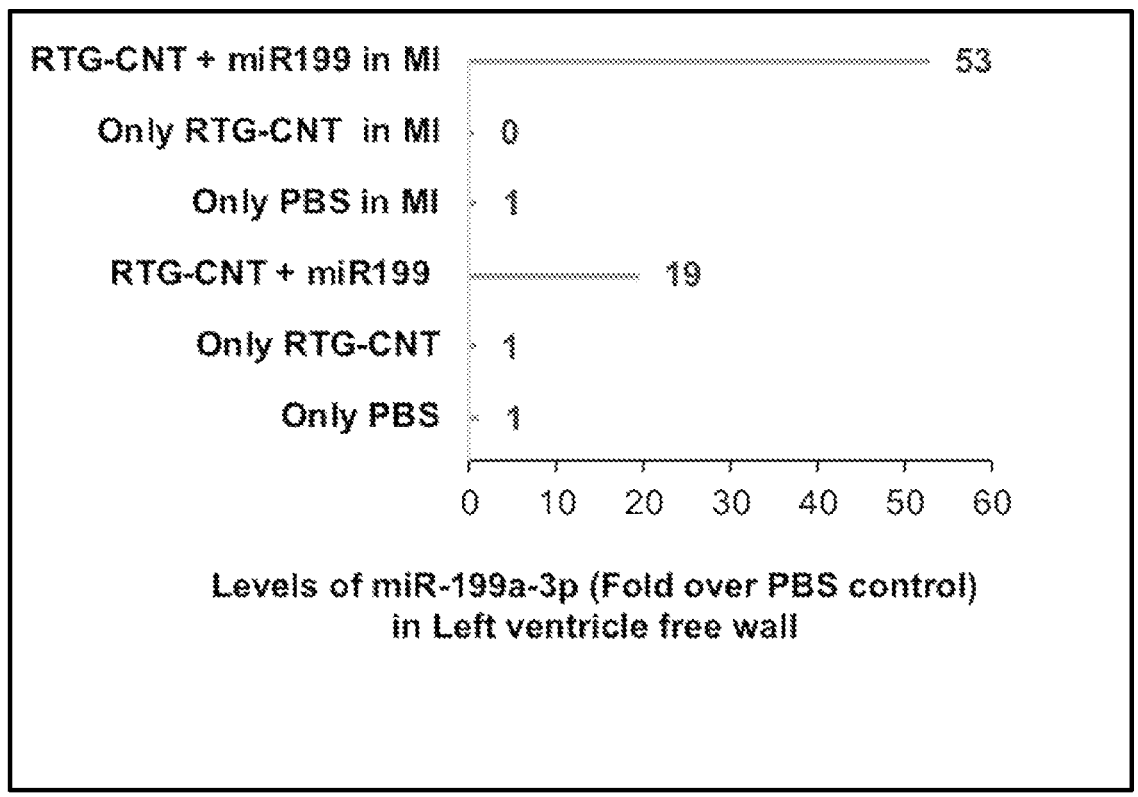

FIG. 26 illustrates the expression of miR-199a-3p in the heart after 7 days post injection.

It will be appreciated that the figures are not necessarily drawn to scale. For example, the dimensions of some of the elements in the figures may be exaggerated relative to other elements to help to improve understanding of illustrated embodiments of the present invention.

DETAILED DESCRIPTION OF EMBODIMENTS OF THE DISCLOSURE

The description of exemplary embodiments of the present disclosure provided below is merely exemplary and is intended for purposes of illustration only; the following description is not intended to limit the scope of the invention disclosed herein. Moreover, recitation of multiple embodiments having stated features is not intended to exclude other embodiments having additional features or other embodiments incorporating different combinations of the stated features.

Various exemplary embodiments of the disclosure provide a carbon nanotube-functionalized reverse thermal gel (RTG) composition that includes a polymer having carbon nanotubes (CNT) attached and optionally one or more bioactive materials and/or a carrier. The additional bioactive materials can be attached to the polymer backbone and/or be in solution or in suspension (e.g., with the carrier). The carbon nanotube-functionalized reverse thermal gel composition can be used to provide a three-dimensional (3D) gel-based matrix shortly after reaching body temperature (or a temperature slightly below body temperature)—i.e., after injection. As set forth in more detail below, the 3D RTG-CNT system supports long-term CMs survival, promotes CMs alignment and proliferation, and improves CMs function and maturation when compared with traditional two-dimensional 2D gelatin controls and 3D plain RTG system without CNT.

Further, the CNT of the composition are thought to be capable of mimicking Purkinje fibers. Purkinje fibers are located in the inner heart ventricular walls, where they work as a conductive system, creating synchronized contractions of the right and left ventricles. The fibrous CNT mesh found in the RTG-CNT composition may be beneficial for promoting more synchronized CMs contractions and, therefore, may help in the electrophysiological and electromechanical host-cell coupling.

In accordance with further exemplary embodiments of the disclosure, the carbon nanotube-functionalized reverse thermal gel composition is a water-soluble material (or soluble in another aqueous diluent, such as PBS or cell culture media) below the composition's gel transition temperature and maintains a solution state at low temperature and turns into a physical gel upon heating (e.g., upon injection—e.g., in or near damaged myocardium). This property allows the composition to be easily injected, while providing desirable mechanical properties after injection.

In accordance with various aspects of exemplary embodiments, the carbon nanotube-functionalized reverse thermal gel composition can transition from liquid a to a gel state at or near a body temperature of a subject (e.g., a human) to be treated. For example, the carbon nanotube-functionalized reverse thermal gel composition can be a liquid or solution at about 25° C. or less and transition from a liquid to a gel at about 30° C. to about 37° C., or at about 29° C., about 30° C., about 31° C., about 32° C., about 33° C., about 34° C., about 35° C., about 36° C., or about 37° C.

An exemplary polymer includes a poly(urea)-polyurethane polymer backbone that is functionalized with one or more CNT. The polymer backbone can be functionalized with, for example, a PNIPAAm functional group to facilitate formation of a reverse thermal gel and/or CNT and/or poly-lysine.

The formula below illustrates an exemplary polymer suitable for forming a carbon nanotube-functionalized reverse thermal gel composition.

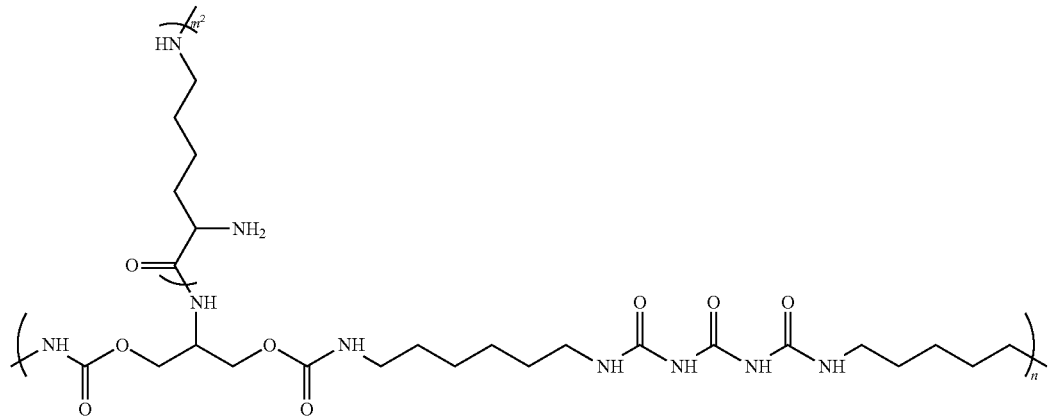

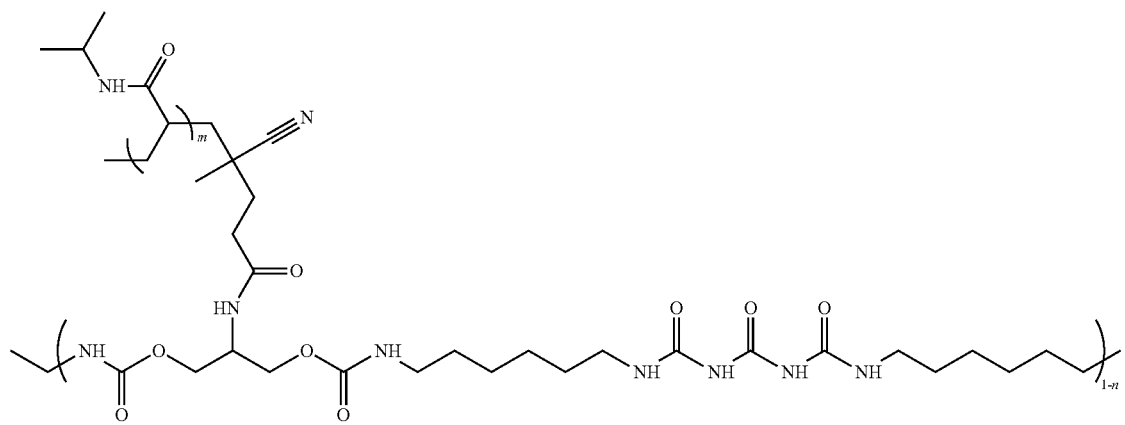

-continued

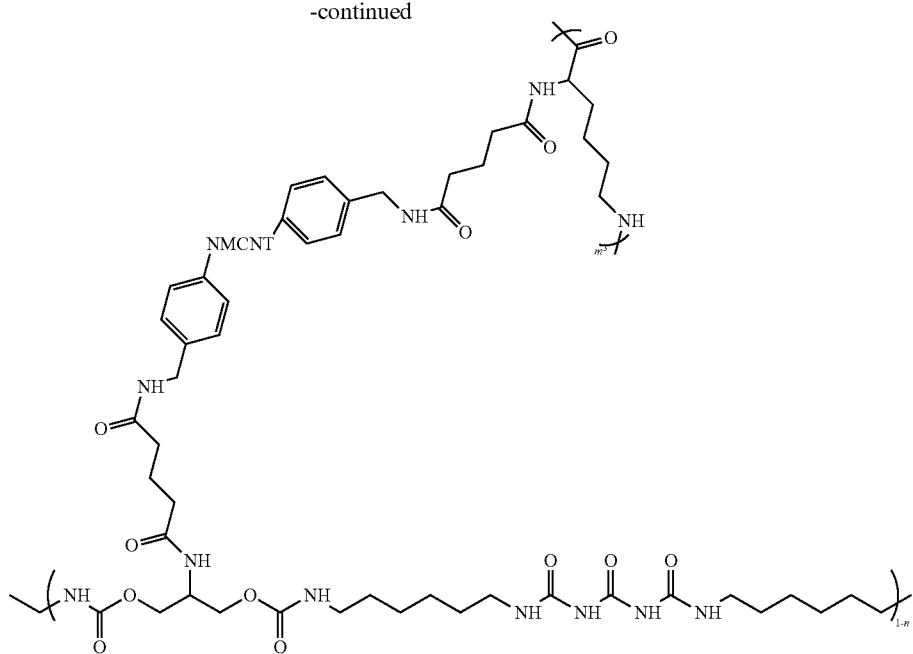

In the above formula, n can range from about 1 to about 18 repeat units; m ranges from 27 to 890 repeat units; m2 and m3 ranges from 5 to 50 repeat units.

A percent of PNIPAAm conjugation can range, for example, from about 5 percent to about 55 percent, or about 10 to about 50 percent, or about 10 to about 45 percent.

Exemplary molecular weights of various components of the polymer and of the polymer are provided below.

Molecular weights of PSHU: 1,500 to 20,000 g/mol.
Molecular weights of PNIPAAm: 3,000 to 100,000 g/mol.
Molecular weights of PSHU-PNIPAAm (RTG): 4,500 to 470,000 g/mol.
Molecular weights of Poly-L-lysine: 500 to 5,000 g/mol.
Molecular weights of PSHU-PNIPAAm-lysine (RTG-lysine): 5,000 to 540,000 g/mol.
Molecular weights of CNT-COOH: 100 to 500 g/mol.
Molecular weights of PSHU-PNIPAAm-lysine-CNT: 8,000 to 550,000 g/mol.
Molecular weights of PSHU-PNIPAAm-lysine-CNT-lysine (RTG-CNT): 9,000 to 555,000 g/mol.

The carbon nanotube-functionalized polymer can be combined with a carrier to form a reverse thermal gel composition. Exemplary compositions can include about 1% (w/w) to about 10% (w/w) of polymer in a carrier, such as an aqueous solvent. Exemplary solvents include water, cell culture media or saline solution.

Figure 1:
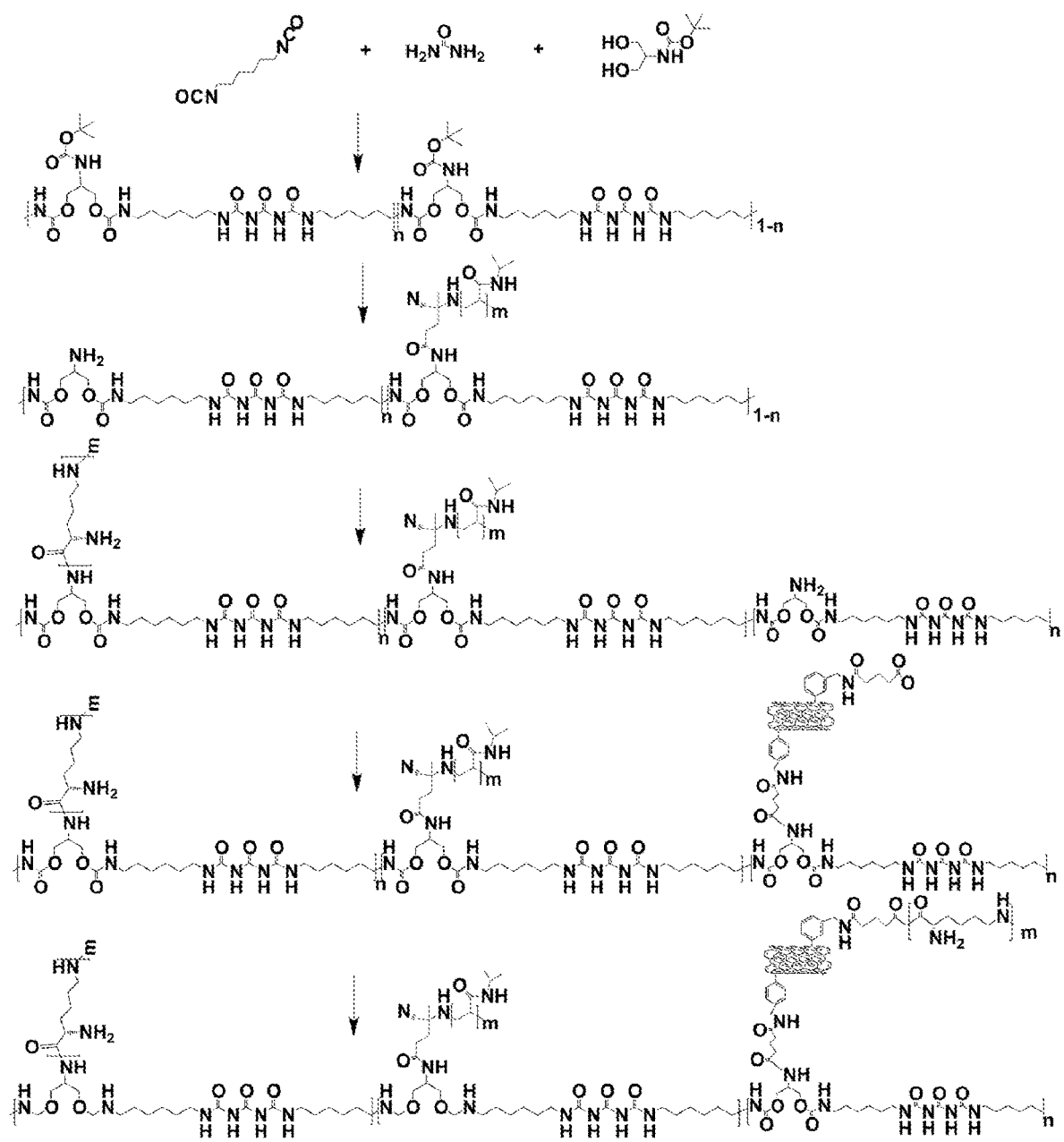
FIG. 1 illustrates a method of forming a polymer suitable for forming a carbon nanotube-functionalized reverse thermal gel in accordance with exemplary embodiments of the disclosure.

Turning now to FIG. 1, an exemplary method of forming a carbon nanotube-functionalized reverse thermal gel composition is illustrated. A suitable polymer for the carbon nanotube-functionalized reverse thermal gel composition can be formed according to steps 1-6 illustrated in FIG. 1. Step 1 includes synthesis of PSHU by reacting urea, N—BOC-serinol and a diisocyanate (e.g., hexamethylene diisocyanate); step 2 includes de-protection of the PSHU; step 3 includes conjugation of PNIPAAm-COOH onto PSHU, which results in PSHU-NIPAAm; the PNIPAAm-COOH can be synthesized by, for example, reacting NIPAAm and a carboxylic acid, such as 4,4'-azobis(4-cyanovaleric acid) (CVA); step 4 includes synthesizing poly-L-lysine and conjugating the poly-L-lysine to the PSHU-NIPAAm; step 5 includes conjugating of CNT (CNT-COOH) to the PSHU-NIPAAm (with poly-L-lysine); and step 6 includes conjugating poly-L-lysine to the CNT. An example of a particular process of forming the polymer is described in more detail below in the context of the specific examples. Exemplary compositions can be formed by forming the polymer as described herein and mixing the polymer with a suitable carrier.

Exemplary diisocyanates suitable for use in synthesizing the polymers for forming a carbon nanotube-functionalized reverse thermal gel composition include, but are not limited to, isophorone diisocyanate, 1,4-phenylene diisocyanate, 1,3-phenylene diisocyanate, toluene-2,4-diisocyanate, toluene-2,6-diisocyanate, 2,4,6-trimethyl-1,3-phenylene diisocyanate, tetramethylene diisocyanate, octamethylene diisocyanate, 1,3-bis(1-isocyanato-1-methylethyl) benzene, 4,4'-methylenebis(phenyl isocyanate), 3,3'-dimethyloxy-4,4'-bisphenylene diisocyanate, 1,8 diisocyanateoctane, $\alpha,\alpha,\alpha'$, $\alpha'$-tetramethyl-1,3-xylylene diisocyanate, and 3,3'-dimethoxy-4,4'-biphenylene diisocyanate.

The reactive groups that can be coupled with amine-containing molecules are common functional groups present on modification reagents. Carboxylic acid (COOH) groups can be easily conjugated in a high yield to primary amines to form amide linkages by EDC/NHS chemistry, as described below. Since the RTG-lysine polymer contains a large number of free primary amine groups, COOH-functionalized CNT can be chemically conjugated with the polymer formed in accordance with the method illustrated in FIG. 1.

Figure 2:
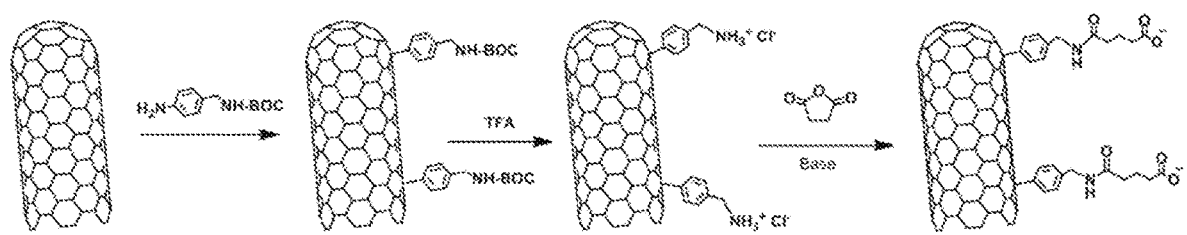
FIG. 2 illustrates an exemplary method of forming functionalized carbon nanotubes in accordance with various embodiments of the disclosure.

FIG. 2 illustrates a method of synthetizing CNT with a COOH group by incorporating amino benzyl groups to MWCNT (e.g., MWCNT purchased from Nanostructured & Amorphous Materials, Inc. (Texas, USA)) via the diazonium salt arylation reaction route. Succinic anhydride was then added to incorporate the COOH groups. A more detailed example of an exemplary method to form CNT functionalized with COOH is described in more detail below.

Figure 3:
FIG. 3 illustrates different MWCNT-COOH dispersed in DMF. From left to right: commercial MWCNT-COOH and MWCNT-COOH synthesized in accordance with exemplary embodiments of the disclosure.
Figure 3:

CNT often produce mixtures of solid morphologies that self-associate into aggregates. In order to have an optimal conjugation of CNT to polymeric materials, it is desirable to achieve a uniform dispersion of CNT in solvents, especially after their functionalization. A technique for forming the dispersion is described above by incorporating amino benzyl groups to MWCNT via the diazonium salt arylation reaction route as further discussed in connection with the specific examples. The obtained CNT-COOH dispersion in DMF was achieved as illustrated in FIG. 3.

Specific Examples

The following non-limiting examples illustrate exemplary polymers, compositions, and uses in accordance with various embodiments of the disclosure. These examples are merely illustrative, and it is not intended that the invention be limited to the examples. Compositions in accordance with the present disclosure may include the specific polymers and other compounds listed below as well as additional and/or alternative materials, compounds, and other constituents.

Materials and Methods

Materials: N-Isopropylacrylamide (NIPAAm), anhydrous N,N-dimethylformamide (DMF), 4,4'-azobis(4-cyanovaleric acid) (CVA), urea, N—BOC-serinol, hexamethylene diisocyanate (HDI), diethyl ether, trifluoroacetic acid (TFA), dichloromethane (DCM), N-(3-dimethylaminopropyl)-N'-ethylcarbodiimide hydrochloride (EDC-HCl), and L-lysine monohydrochloride were purchased from Sigma-Aldrich, (St. Louis, Mo., USA). N-Hydroxysuccinimide (NHS) was purchased from Alfa Aesar (Ward Hill, Mass., USA). MWCNT were purchased from Nanostructured & Amorphous Materials, Inc. (Texas, USA), and all reagents used for the MWCNT functionalization were purchased from Sigma Aldrich. The filters for MWCNT purification were purchased from Millipore JHWP filters (0.45 µm).

Equipment: Morphological characterization was carried out by scanning electron microscopy (SEM) using a JSM-6010LA (JEOL, Tokyo, Japan). Samples were prepared as follows: the polymers in solution (1% w/w) were allowed to form a gel at 37° C. Warm water was then put on top and the samples were frozen immediately by liquid nitrogen immersion. The frozen samples were then lyophilized −45° C. for 48 h and analyzed by SEM. The storage and loss moduli were measured using an Ares 4400 rheometer (TA Instruments) with an 8 mm parallel plate geometry. A temperature ramp was performed from 25° C. to 45° C. at a ramp rate of 2° C. at a constant strain rate of 1.0 rad s-1 at 0.5% stain (within the viscoelastic regime) to determine gelation as a function of temperature. Experiments were performed in triplicate and averaged. Thermogravimetric analyses (TGA) were performed under a nitrogen flow (60 ml min-1) using a TA Instruments Q500 on sample sizes from 0.7 to 1 mg, and the mass was recorded as a function of temperature. The samples were heated to 100° C. for 20 min and then to 800° C. at 10° C. min-1. Data was interpreted using Thermal Advantage v1.1A software. TEM analyses were performed with a Philips EM 208 microscope with an accelerating voltage of 100 kV (images were acquired using an Olympus Morada CCD camera). CNT samples were typically suspended in DMF with the help of sonication, and these suspensions were drop-casted on copper or nickel grids (diameter=3.00 mm, 200 mesh, coated with carbon vacuum overnight, prior to the TEM analysis). Conductivity measurements were performed using a four-probe configuration with a Jandel resistivity meter (RM-3000) linked with a Jandel four-point probe. Resistance measurements were taken with a Protek 6100 multimeter. Briefly, 400 µl of 1.5% (w/w) polymeric solution dissolved in ultrapure water was allowed to gel at 37° C. for 2 min in a 1×1 cm mold. Resistance measurements were performed 3 times for each gel and measurements were collected in several different areas in the gel. Ultra-pure water was used to avoid external ions that may interfere in the material resistance. Resistance measurements were also recorded for CNT-COOH suspended in 400 µl of ultrapure water. Viscosity measurements were carried out by using a cone-and-plate digital viscometer (CAP2000+; Brookfield) at 15° C., 30 s runtime. Dry RTG-lysine or RTG-CNT were dissolved in growth NRVM media at 1.5% (w/w) and then measured in triplicate at a shear rate of 900 RPM. The viscosity of growth media was also analyzed under the same conditions.

CMs grown on 3D scaffolds for 21 days were characterized for their beating using Atomic Force Microscopy (AFM) JPK NanoWizard® 4a, (JPK Instruments USA, Carpenteria, Calif.) with a petri dish heater. Briefly, the gel samples were allowed to come back to solution by letting the sample remain at room temperature for 5 min. The polymer solution was then removed and the sample was washed with warm media. The cells that migrated to the plate bottom were then analyzed by AFM, by approaching a triangular cantilever with a gold colloidal probe glued at its apex (CP—Au-PNPL-5, NanoandMore) until a force of 0.5 nN was reached. Calibration of the cantilever was made applying the thermal noise method. Beating height was measured for 2.5 s keeping the force exerted by the cantilever as constant.

MWCNT Functionalization: 200 mg of amino benzyl functionalized carbon nanotubes with a loading of amino groups of 250 µmol g-1 were suspended in 200 ml of NaOH 1M (pH 8) and 20 mg of succinic anhydride were added. The suspension was stirred at room temperature for 16 h, and was then filtered on Millipore JHWP filters (0.45 µm) and washed several times with water to neutrality and then with methanol and diethyl ether. The dried powder weighted 205 mg. The powder was characterized by TGA, Kaier test and TEM.

Polymer Synthesis: With reference again to FIG. 1, PSHU was synthetized by reacting N—BOC-serinol (1.147 g, 6 mmol), urea (0.36 g, 6 mmol) and HDI (2.018 g, 12 mmol) for 7 days at 90° C. under a nitrogen atmosphere. Anhydrous DMF (6 ml) was used as solvent. The mixture was precipitated into excess anhydrous diethyl ether three times. Unreacted urea was removed by water, and the polymer was lyophilized at −45° C. for 48 h. PSHU was de-protected using 30 ml of TFA/DCM (1:1, v/v) mixture. The de-protection reaction was performed for 45 min at room temperature. The resulting polymer was purified by three precipitations into diethyl ether. PNIPAAm-COOH was synthetized by reacting NIPAAm (5 g, 800 mmol) and CVA (0.06 g, 4 mmol) for 3 h at 68° C. under nitrogen atmosphere. Anhydrous DMF (10 ml) was used as solvent. The mixture was precipitated into hot water (60° C.). The polymer was then dissolved in ultrapure water and dialyzed (MWCO: 12,000-14,000 Da) for 5 days. The conjugation of PNIPAAm-COOH onto PSHU—NH2 was performed as follows: PNIPAAm-COOH (0.75 g, 1.21 mmol) was dissolved in 5 ml of anhydrous DMF with five molar excess of EDC-HCl and NHS at room temperature under a nitrogen atmosphere for 24 h. 1 ml of PSHU—NH2 solution (0.125 g ml-1) prepared in anhydrous DMF was added and the reaction was performed for 48 h at room temperature under a nitrogen atmosphere. The mixture was precipitated into excess diethyl three times. The polymer was then dissolved in ultrapure water and dialyzed (MWCO: 12,000-14,000 Da) for 5 days at room temperature and then filtered through a 2 µm filter. The filtered solution was lyophilized at −45° C. for 48 h. Poly-L-lysine was synthetized by dissolving L-lysine (0.034 g, 5 mmol) in 5 ml of PBS with five molar excess of EDC-HCl and NHS in a 25 ml round bottom flask. The mixture was stirred for 15 min at 4° C. A 10 ml of PSHU-PNIPAAm solution (0.1 g ml-1) prepared in PBS was added drop-wise and the reaction was performed for 48 h at room temperature. The polymer was dialyzed (MWCO: 12,000-14,000 Da) for 5 days at room temperature and then filtered through a 2 µm filter. The filtered solution was lyophilized at −45° C. for 48 h. For the CNT conjugation, 300 mg of CNT-COOH were dissolved in 15 ml of anhydrous DMF and sonicated for 30 min. Twenty molar excess of EDC-HCl and NHS were then added and the mixture was stirred for 15 min at room temperature. 5 ml of RTG-lysine solution (0.1 g ml-1) prepared in anhydrous DMF was added drop-wise and the reaction was performed for 48 h at room temperature. To remove unreacted CNT-COOH, the mixture was centrifuged 5 firms at 4000 rpm at 4° C. Then, the polymer was dialyzed (MWCO: 12,000-14,000 Da) for 5 days at room temperature and lyophilized at −45° C. for 48 h. (0.034 g, 15 mmol) L-lysine was then added to cover the remained COOH groups of the CNT. L-lysine was dissolved in 5 ml of PBS with five molar excess of EDC-HCl and NHS. The mixture was stirred for 15 min at 4° C. At the same time, the COOH groups of the CNT conjugated to the RTG-lysine, were activated with five molar excess of EDC-HCl and NHS. The mixture was stirred for 15 min at 4° C. The activated L-lysine was then added drop-wise to the CNT-RTG and the reaction was performed for 48 h at room temperature. The polymer was dialyzed (MWCO: 12,000-14,000 Da) for 5 days at room temperature and then lyophilized at −45° C. for 48 h.

Neonatal rat ventricular myocytes (NRVMs) culture: NRVMs were prepared from six, 1-day old, pups. All animal studies were performed according to the guidelines of the University of Colorado Denver Animal Care and Use Committee. Briefly, ventricles were separated from the atria using scissors and then dissociated in calcium and bicarbonate-free Hanks with Hepes (CBFHH) buffer containing 500 mg ml-1 of collagenase type 2 (Worthington, Biochemical Corporation), and 1 mg/ml of pancreatin. Cardiomyocytes were enriched (>90% purity) over non-myocytes by two sequential pre-plating steps on 100-mm dishes in MEM, 4.5 g supplemented with 5% bovine calf serum and 2 mg ml-1 vitamin B12 and cultured. Unattached cells (predominantly myocytes) were collected and cultured in 2D gelatin coated dishes and into 3D polymeric matrices and then subjected to the different treatments and subsequent analyses. All experimental conditions were tested in triplicate on at least 3 independent cell cultures.

3D in vitro cell culture: In vitro 3D culture experiments were performed with the freshly isolated NRVMs by mixing 9×104 cells with 150 µl of polymeric solution and allowing the solution to form a gel at 37° C. Then 100 µl of warm cell culture medium was added on top. Triplicates from at least 3 independent experiments were analyzed for this study.

Immunocytochemical staining: Immunocytochemistry was performed after 8, 14 and 21 days of culture using the cardiac-specific marker α-sarcomeric actinin 1:100 (SIGMA) to assess the contractile apparatus of CMs, vimentin 1:100 (abcam) a cytoskeleton marker commonly used for fibroblast staining and CD31 1:100 (abeam) as marker for endothelial cells. Goat anti-mouse antibody conjugated to Alexa Fluor 488 (Invitrogen), goat anti-chicken Cy5 (abcam) and goat antirabbit antibody conjugated to TRITC (sigma) were used as secondary antibodies at 1:300. Connexin 43 1:100 (sigma) was assessed at 21 days to determine the gap junction area between CMs. Goat anti-rabbit antibody conjugated to Alexa Fluor 594 was used as secondary antibody 1:300 (Invitrogen). 3D and 2D (control) cell cultures were washed twice with warm PBS 1× and then fixed in warm PBS containing 4% PFA for 15 min at 37° C. Cells were permeabilized with warm 1% Triton X-100 for 1.5 h, blocked in warm 2% BSA in PBS (blocking buffer) for 45 min, and incubated with primary antibodies overnight (all the steps were performed at 37° C.). Secondary antibodies were incubated for 45 min at 37° C. Cell nuclei were stained with DAPI and samples were mounted in Vectashield (Vector Laboratories). When indicated and 12 h prior to analysis, cells were further processed using the Click-IT EdU 555 Imaging kit (Life Technologies) to reveal EdU incorporation, according to the manufacturer's instructions, and stained with DAPI. Fluorescent images were taken from 4 regions of each sample (n=3) with a Zeiss LSM780 spectral, FLIM, 2P, SHG confocal. Within each experiment, instrument settings were kept constant. To assess the electrical activity of CMs growing in the 3D CNT-RTG and controls, after 21 days of culture, intracellular calcium signaling of CMs were recorded. Cell-permeant fluo 4, AM was added, according to manufacture instructions, to each sample and incubated for 15 min for 2D control groups and 30 min for 3D polymeric groups. Samples were washed 3 times with warm media before imaging. Calcium transients during spontaneous beating of CMs was recorded using a Zeiss LSM780 confocal and was measured for 20 s. Experiments were performed in triplicate from 3 independent experiments and averaged. Data was corrected for background epifluorescence.

RNA/DNA Isolation and Quantitative RT-PCR (qPCR): Total RNA and DNA purified from cultured neonatal rat cardiomyocytes at 21 days after culture were isolated using the Trizol-method (Invitrogen) and quantified by spectrophotometry. cDNA was prepared from 1 µg total RNA by reverse transcription with MMLV-RT (Invitrogen) utilizing random hemmer primers (Invitrogen) following standard protocols (Invitrogen). RNA expression levels for beta-myosin heavy chain (βMHC), alpha-myosin heavy chain (RMHC), A-type natriuretic peptide (ANP) sarcoplasmic reticulum Ca2þ ATPase 2a (SERCA2a) and brain natriuretic peptide (BNP) were quantified with real-time TaqMan reverse transcriptase (RT)-PCR using C1000 CFX96 Real-Time System (Bio-Rad). TaqMan reactions were carried out in 96-well plates using cDNA, TaqMan universal PCR master mix, predesigned and pre-optimized TaqMan. Gene expression assays, including specific primers and fluorescent probes were performed according to manufacturer's instructions. GAPDH mRNA was used as an endogenous control. Each set of primer pairs was obtained from the Applied Biosystems catalogue for quantitative gene expression analysis of the specific genes of interest. RT and template controls were used to monitor for any contaminating amplification according to manufacturer (Applied Biosystems). We used the following temperature protocol: 3 min at 95° C., 10 min at 95° C., and 30 min at 60° C. followed by 39 cycles of 10 s at 95° C. and 30 s at 60° C. GAPDH expression was similar in all study groups and was therefore employed to normalize for differences in RNA quantity and RT-efficiency.

In vivo pilot biocompatibility test: In vivo studies were performed in C57 black 6 male mice. All animal studies were performed according to the guidelines of the University of Colorado Denver Animal Care and Use Committee. Briefly, a left thoracotomy was carried out via the fourth intercostal space. 30 µl of either polymeric solution (RTG-CNT or RTG) or saline solution were injected in 3 different spots (10 µl per spot) around the apical, proximal, lateral, and septal LV wall regions through a 32-gauge needle. After injections, the thoracotomy site was closed and the animals were allowed to recover. The animals were followed for 2, 4 and 8 weeks.

mRNA transfection using the RTG-CNT polymer as delivery system. fluorescent labeled mRNA was mixed with 1 ml of RTG-CNT polymeric solution (1.5% w/w) at 4° C. The resultant solution was then mixed with $6 \times 10^5$ neonatal rat ventricular cardiomyocytes (NRVM). The samples were incubated at 37° C., to allow gel formation. Then warm cell culture medium was added on top. The final concentration of encapsulated miRNA was 25 nM per sample. Samples were analyzed after 72 hr.

Statistical analysis: For all proposed experiments, data was collected in triplicate from ≥3 independent experiments. ImageJ was used for cell counting in 10 fields per each condition. For calcium transients, signals from myocytes were collected and analyzed from 10 fields per sample and averaged. For the AFM measurements, data were acquired from ≥10 cells per sample and averaged. Statistical significance between experimental groups was determined using ANOVA. ANOVA Power analysis was completed using GraphPad Prism7software. A p value of <0.05 was considered statistically significant.

Results and Discussion

The above techniques were used to develop a conductive RTG-CNT polymer that supports CMs survival, maturation, and proliferation, and also possesses the advantages of an injectable RTG.

Figure 4:
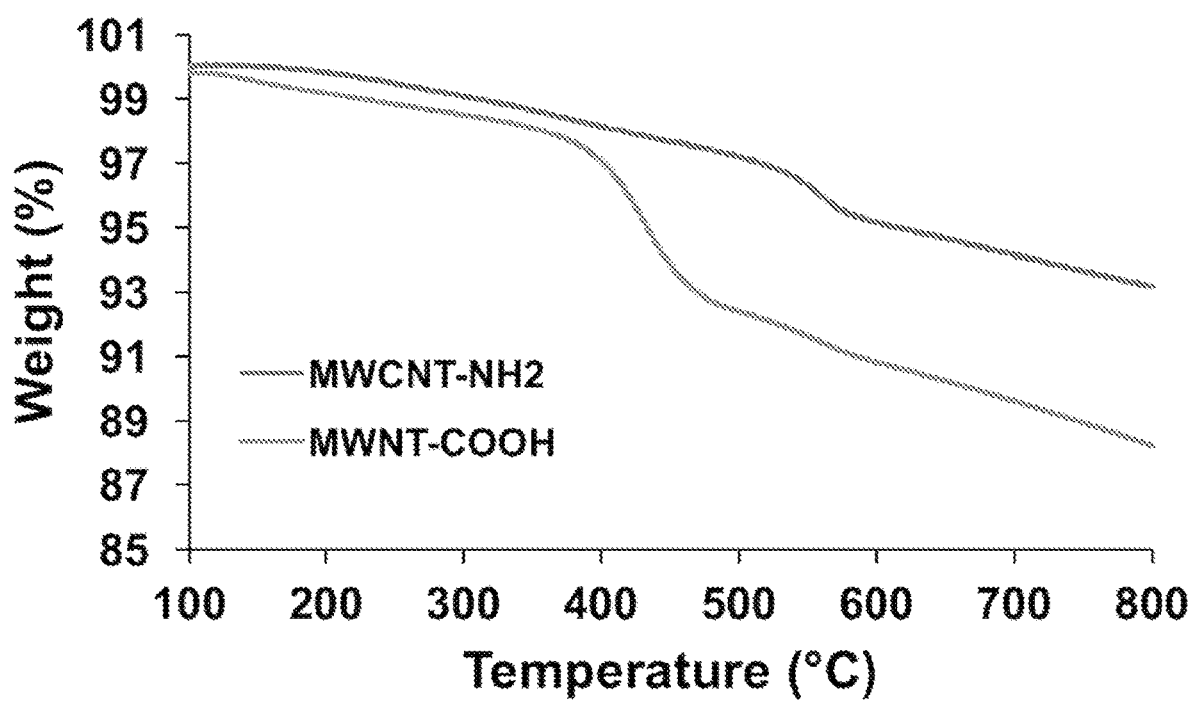
FIG. 4 illustrates the incorporation of COOH groups in an amino benzyl functionalized CNT as demonstrated by thermogravimetric analysis (TGA) in accordance with various embodiments of the disclosure.

The incorporation of COOH groups in the amino benzyl functionalized CNT was demonstrated by thermogravimetric analysis (TGA) of MWCNT-NH2 (402) and MWCNT-COOH (404), as illustrated in FIG. 4. The results show a larger weight loss after the reaction with succinic anhydride and the following purification, with a yield of 320 µmol of COOH groups per gram of material. The Kaiser test revealed a residual amount of 25 µmol/g free amino groups, where the initial loading of amino groups was 345 µmol/g, indicating that COOH groups were incorporated into 92.7% of the CNT by mass. This high percentage of COOH in the CNT is ideal to facilitate the chemical conjugation with the RTG-lysine.

Figure 5:
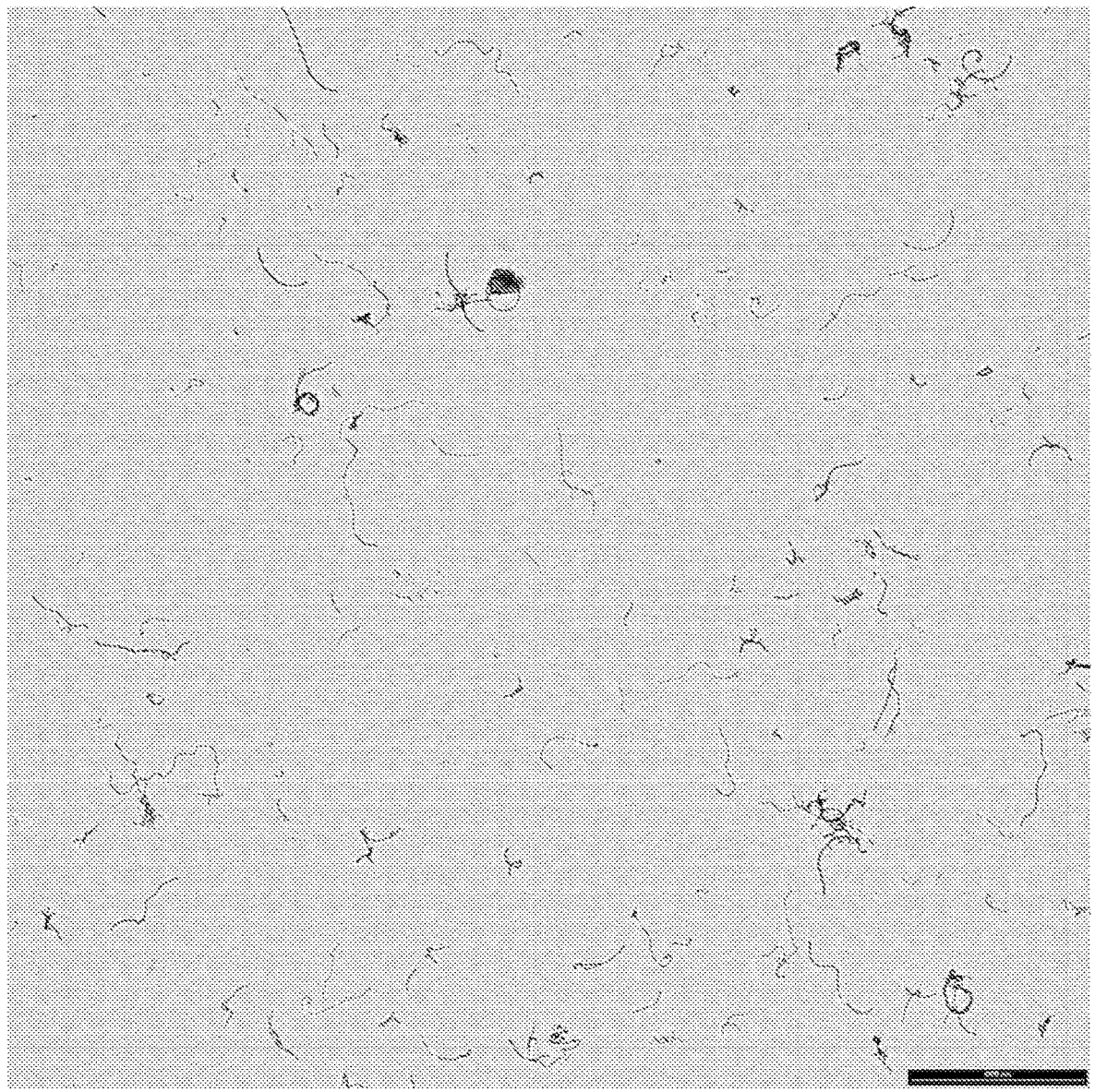
FIG. 5 illustrates a transmission electron micrograph illustrating multi-welled carbon nanotubes dispersed in a solvent in accordance with various embodiments of the disclosure.

The dispersion of CNT-COOH in dimethylformamide (DMF) was analyzed by transmission electron microscopy (TEM). FIG. 5 illustrates that the CNT-COOH were well dispersed in the solvent which is ideal for further conjugations. The solubility of MWCNT-COOH in DMF was then compared with commercial oxidized MWCNT-COOH (sigma) as shown by FIG. 3. The commercial oxidized CNT agglomerate and adsorbed the DMF solvent even after 30 min sonication. On the other hand, CNT-COOH as described herein were well dispersed in DMF under the same conditions (30 min sonication at room temperature).

Figure 6:
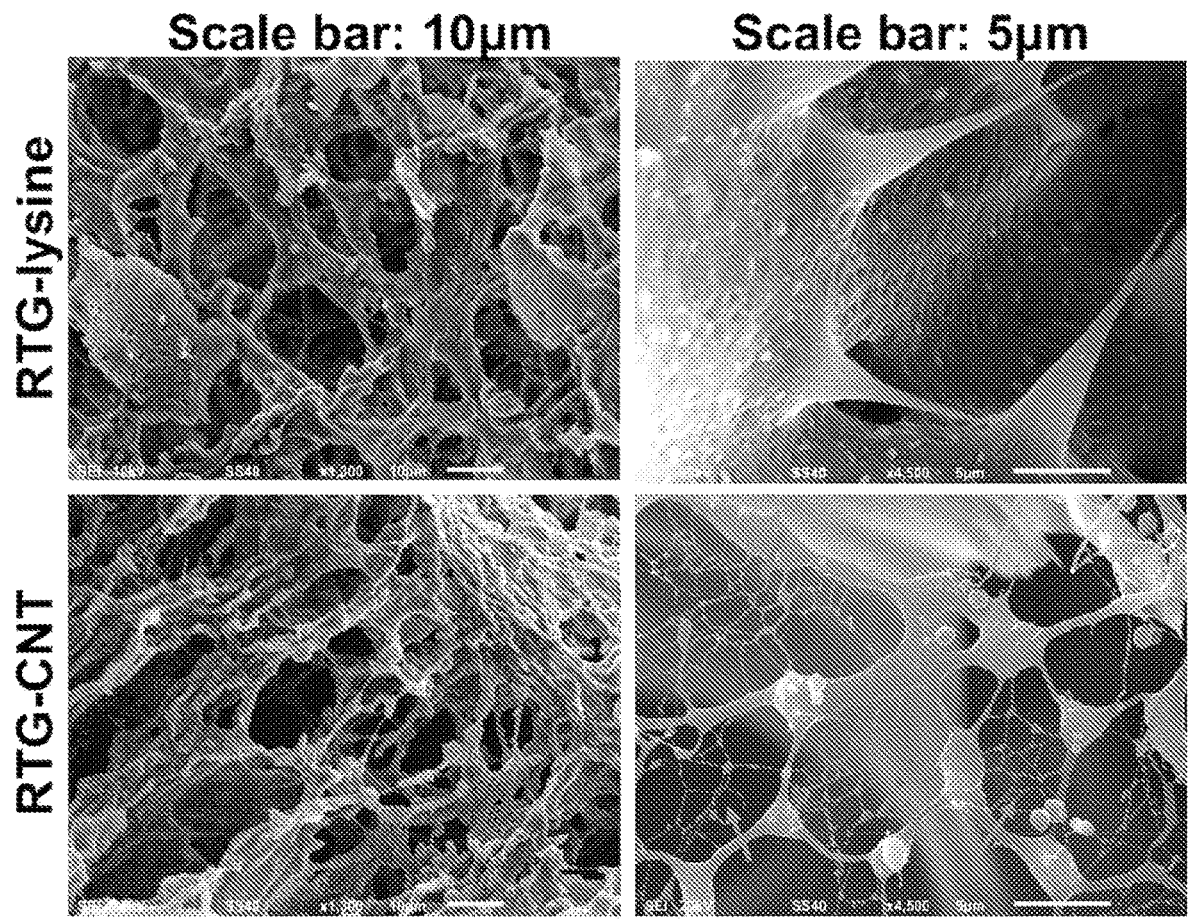
FIG. 6 illustrates cross section micrographs of RTG systems at different magnifications in accordance with various embodiments of the disclosure.

The 3D morphological characterization of both RTG-lysine and RTG-CNT was performed by scanning electron microscopy (SEM). Cross-sectional images of the 3D structure, as illustrated in FIG. 6, revealed a highly porous configuration with interconnected porous structures in both RTG systems. Both appeared to have similar porosity regarding pore size and pore distribution, but the RTG-CNT system presents a fibrous mesh of CNT among the pores (FIG. 6, bottom right panel).

Figure 7:
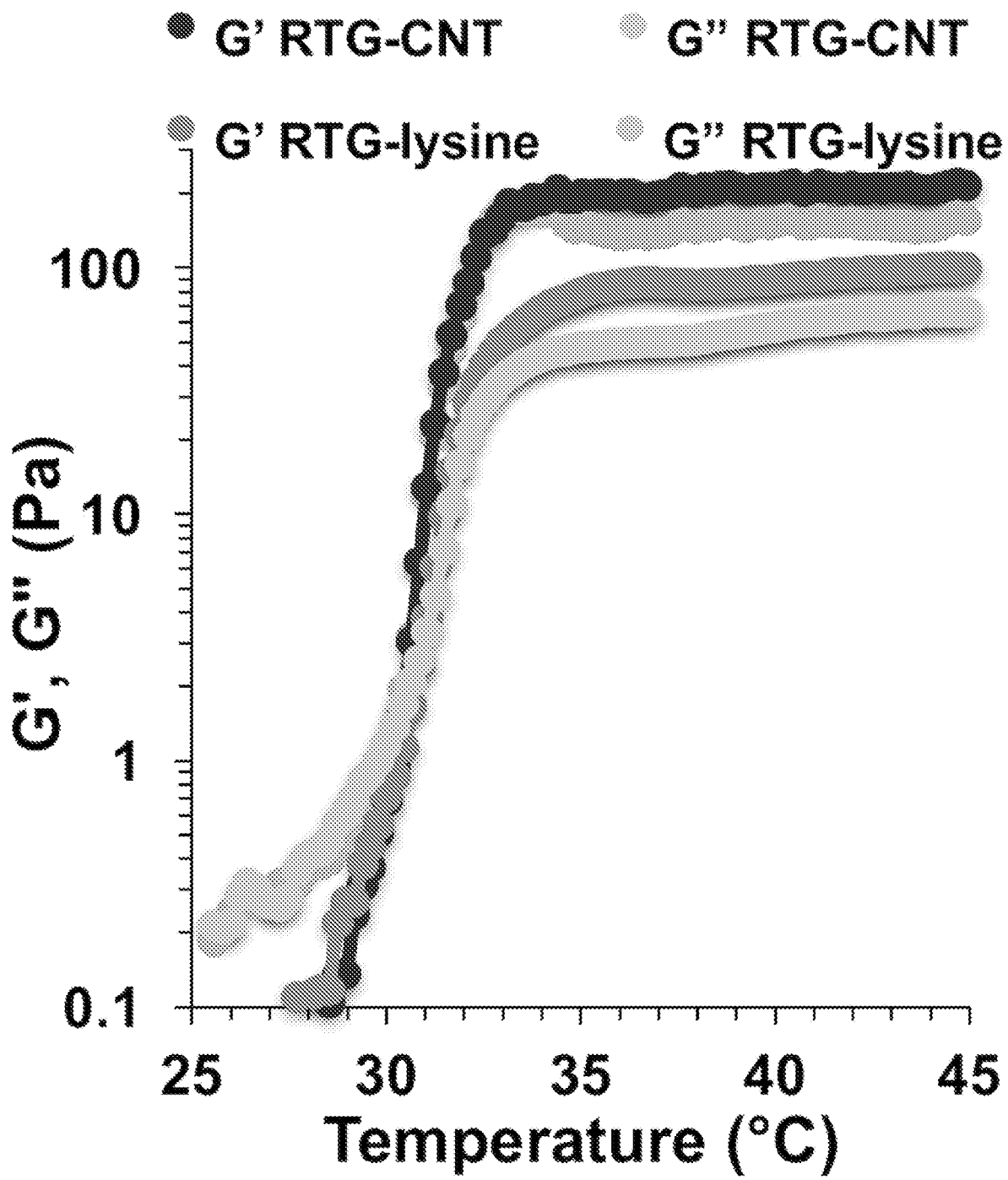
FIG. 7 illustrates storage and loss moduli of both RTG-lysine and RTG-CNT and temperature-dependent phase transition in accordance with various embodiments of the disclosure.
Figure 8:
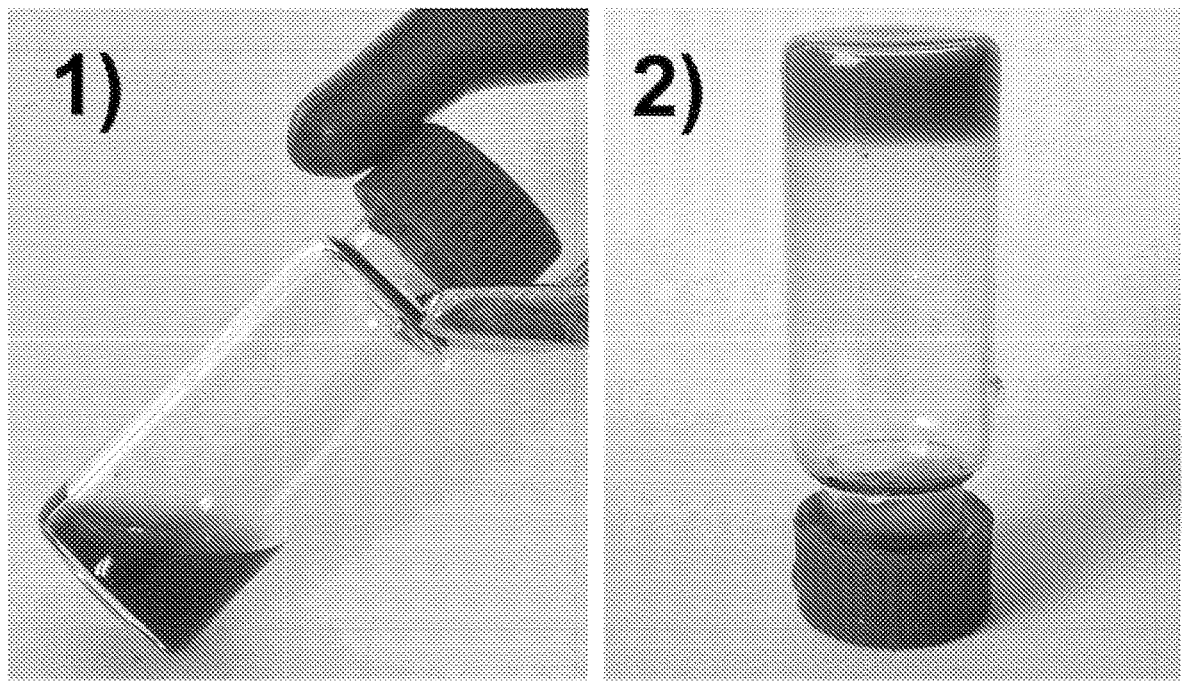
FIG. 8 illustrates (1) an aqueous solution of RTG-CNT at room temperature (2) RTG-CNT physical gel at 37° C. in accordance with additional embodiments of the disclosure.

The sol-gel phase transition and the storage and loss moduli of both RTG-lysine and RTG-CNT were determined using oscillatory shear rheometry, as illustrated in FIG. 7, where 702 represents G' RTG-CNT, 704 represents G' RTG-lysine, 706 represent G" RTG-CNT, and 708 represents G' RTG-lysine. The solution to gel phase transition was measured using a temperature sweep and determined to be at approximately 31° C. for gels with and without CNT, which is near body temperature and ideal for biomedical applications. RTG gels with and without CNT have viscoelastic properties at 37° C., where the RTG-CNT presented higher moduli (G'=221±24.6 Pa, G"=146±21.6 Pa) than the RTG-lysine (G'=82.0±4.2 Pa, G"=48.7±2.2 Pa). Therefore, the chemical conjugation of CNT improves the mechanical properties of the RTG system/composition. Although, the polymer concentration tested makes gels with low stiffness, we have found that increasing the polymer concentration in solution, increases the mechanical properties of RTG systems, which may be beneficial to provide mechanical support to the wounded heart. FIG. 8 illustrates 1) an aqueous solution of RTG-CNT at room temperature 2) the solution turned to a physical gel at 37° C.

Electrical characterization of both the RTG-lysine and RTG-CNT systems was carried out by conducting resistance measurements, as illustrated in FIG. 9. The RTG-lysine system exhibited a higher resistance at 37° C. than the RTG-CNT and the CNT-COOH in nano pure water (RTG-lysine: 236.8 KΩ±3; RTG-CNT 144.3 KΩ±4.3; MWCNT-COOH 24.3 KΩΩ±0.64), indicating that the RTG-CNT and CNT-COOH have greater conductance compared to the RTG-lysine. As expected, the CNT-COOH had the lowest resistance, agreeing with previously published studies, while the RTG-CNT had a resistance in between the RTG-lysine polymer and the CNT-COOH.

Due to the interest of using the RTG-CNT system for cell delivery, viscosity analysis of both RTG-lysine and RTG-CNT systems were also performed and compared with cell culture media. FIG. 10 shows that both RTG-lysine and RTG-CNT solutions at 1.5% present low viscosity which is beneficial for polymer injection. (RTG-lysine: 16.78±1.2 mPa·s; RTG-CNT: 13.4±2.5 mPa·s; media: 21.9±0.8 mPa·s).

The RTG-CNT, which not only had a higher conductance but also presents better mechanical properties in term of stiffness than the RTG-lysine, and has a low viscosity, holds great promise for use as an injectable material for cardiac tissue engineering.

In vitro long-term NRVMs survival: NRVMs cultured in 3D using an RTG-lysine system have improved survival, function and proliferation, all in comparison to traditional 2D gelatin-coated culture-plate and plain RTG. Therefore, we used the RTG-lysine system as a 3D control to assess the biological effects of the RTG-CNT scaffold on NRVMs. Traditional 2D gelatin coating culture dishes, broadly used for NRMV culture and prepared as previously described, were also used as controls.

The organization and phenotype of the NRVMs cultured in 3D using the RTG scaffolds were investigated by immunocytochemistry. Staining for α-sarcomeric actinin, a protein involved in cardiac muscle contraction, was used as cardiac-specific marker. Staining for vimentin, a cytoskeletal fibroblast protein was used to identify fibroblasts, which typically comprise around 10% of the cell population within our NRVMs isolation protocol. See, Martinelli, V.; Cellot, G.; Fabbro, A.; Bosi, S.; Mestroni, L.; Ballerini, L. Improving Cardiac Myocytes Performance by Carbon Nanotubes Platforms. Front. Physiol. 2013, 4 SEP (September), 1-6. And Martinelli, V.; Cellot, G.; Toma, F. M.; Long, C. S.; Caldwell, J. H.; Zentilin, L.; Giacca, M.; Turco, A.; Prato, M.; Ballerini, L.; Mestroni, L. Carbon Nanotubes Instruct Physiological Growth and Functionally Mature Syncytia: Nongenetic Engineering of Cardiac Myocytes. ACS Nano 2013, 7 (7), 5746-5756. CD31 was used as a marker for endothelial cells, which are not normally present in the CMs preparation protocol noted above.

As expected, no positive CD31 cells were observed in the cultures. On the other hand, fluorescence microscopy revealed a clear cardiac sarcomere structure represented by cross-striations in NRVMs grown in 3D using both RTG systems (FIG. 11). Even though some fibroblasts were observed in both polymeric scaffolds, most of the cells are CMs as shown by their α-actinin-positive cardiac phenotype during all time points (FIG. 12). In addition, a greater percentage of cells in the RTG systems were α-actinin-positive compared to cells cultured on the 2D gelatin controls. In contrast, the number of fibroblasts significantly increased in the 2D gelatin-controls compared with the polymeric systems (FIG. 13). Although the original culture percentage of fibroblast increased in the polymeric systems, it is clear that the polymeric matrix suppresses their long-term proliferation capacity compared with the 2D gelatin controls as has been reported previously. In addition, the microporous architecture of the 3D carbon nanotube-functionalized reverse RTG scaffolds promotes cellular alignment and elongation of both CMs and fibroblasts, which is beneficial for both CMs maturation and improved cell contractility. On the other hand, when comparing the two RTG systems, the percentage of cells that were α-actinin-positive remained nearly constant for all the times points except at day 8, when this value was significantly increased in the RTG-CNT system.

Although most investigations focus on the study of CMs for cardiac tissue remodeling, fibroblasts and endothelial cells are also desired to mimic the native cardiac tissue. Fibroblasts have important functions in the myocardium including electrical coupling with cardiomyocytes, and propagation of electrical stimuli. Endothelial cells are generally required for vascularization. Even though we were not able to find endothelial cells in our cultures, the fact that we can perform a co-culture of both CMs and cardiac fibroblast in 3D holds tremendous potential as an emerging artificial cardiac tissue.

The proliferation capacity of NRVMs cultured in the RTG systems and on 2D gelatin controls was analyzed. Cells were analyzed using a 5-ethynyl-2'-deoxyuridine (EdU) proliferation assay in complete medium at 2, 3, and 4 days post-seeding. EdU is an easy and highly sensitive method to label newly synthetized DNA of proliferative cells. In addition, EdU has similar profiles and rates of cell proliferation as other traditional methods, such as BrdU (Sun, X.; Zhang, C.; Jin, H.; Sun, G.; Tian, Y.; Shi, W.; Zhang, D. Flow Cytometric Analysis of T Lymphocyte Proliferation in Vivo by EdU Incorporation. Int. Immunopharmacol. 2016, 41, 56-65) and phosphorylated-histone H3 (pHH3) (Martinelli, V.; Cellot, G.; Fabbro, A.; Bosi, S.; Mestroni, L.; Ballerini, L. Improving Cardiac Myocytes Performance by Carbon Nanotubes Platforms. Front. Physiol. 2013, 4 SEP (September), 1-6 and Martinelli, V.; Cellot, G.; Toma, F. M.; Long, C. S.; Caldwell, J. H.; Zentilin, L.; Giacca, M.; Turco, A.; Prato, M.; Ballerini, L.; Mestroni, L. Carbon Nanotubes Instruct Physiological Growth and Functionally Mature Syncytia: Nongenetic Engineering of Cardiac Myocytes. ACS Nano 2013, 7 (7), 5746-5756), marker of cell division that is only expressed in proliferating cells. We have previously analyzed the effect of CNT in the proliferation capacity of CMs using BrdU and pHH3 as markers of cell division. No differences in terms of cell proliferation rates were observed between both markers. Therefore, since EdU has similar rates of cell proliferation as BrdU and PHH3, it was used to label proliferating cells nuclei, while antibodies for α-sarcomeric actinin and vimentin were used to distinguish between cardiac and fibroblast cells, respectively. All culture systems showed EdU incorporation at all time points (FIG. 14, nuclei—indicated with arrows). On day 2, there were significantly more proliferating α-sarcomeric actinin-positive cells in the RTG-lysine, (39%±17.3) than in the RTG-CNT system (15.76%±1.27) or on the 2D gelatin controls (8.9%±2.1) based on the number of EdU-positive cells (FIG. 15). However, at day 3, the percentage of EdU-positive NRVMs increased to 23.3%±7 in the CNT-RTG system. On the other hand, the amount of proliferative NRVMs decreased on the RTG-lysine system to 9.6%±4 at day 3. The percentage of proliferative NRVMs growing on gelatin control remained constant at day 3 (6±3). The percentage of EdU- and α-sarcomeric actinin-positive cells progressively decreased over time, reaching the lowest levels for each system at day 4 (2D gelatin controls: 3.8%±1; RTG-lysine: 5.0%±1.3; RTG-CNT: 15.8%±1.6). Since the regenerative capacity of CMs after injury is generally insufficient for complete heart restoration and because the RTG-CNT system appears to improve the percentage of cardiac cell proliferation in culture over time, this system could be potentially beneficial to promote proliferation of both transplanted CMs and CMs from the native tissue. On the other hand, a significant increment of dividing fibroblast (FIG. 16) was observed at day 2 on the gelatin controls compared with the RTG-CNT and the RTG-lysine systems. No significant differences of dividing fibroblast were observed at day 3 and 4 between the samples.

Since intercellular communication are important organizational features of the heart, we investigated the levels and localizations of the gap-junctions through immunostaining for connexin 43 (Cx43), after cells had been cultured in the RTG-CNT system for 21 days and then compared with 2D gelatin controls and cell cultured in the 3D RTG-lysine. The area of Cx43 in α-actinin-positive cells was quantified by image J. FIG. 17 shows representative images of NRVMs stained for Cx43 and α-actinin after 21 days of culture in the RTG systems and on 2D gelatin controls. As shown in FIG. 18, we found that NRVMs cultured in the RTG-CNT had the greatest Cx43-positive area (1.87 µm2±0.36) when compared with 2D gelatin controls (0.25 µm2±0.1) and the RTG-lysine system (0.88 µm2±0.13). As expected, NRVMs cultured in the RTG-lysine system also had a significantly greater Cx43-positive area compared with the 2D gelatin controls. Several studies have indicated that Cx43 organization is crucial for normal ventricular function and cellular impulse propagation in the healthy human heart. On the other hand, alteration of the Cx43 organization may be one of the main mechanisms leading to arrhythmias. Therefore, the fact that the RTG-CNT systems promote a more organized area of Cx43 expression may be beneficial in improving the function and integration of transplanted CMs with the host and for the development of functional syncytia.

It has been reported that organized spontaneous intracellular calcium oscillations are correlated with CMs maturation and cell function. To investigate cellular cardiac function, we imaged spontaneous calcium transients to assess NRVMs electrical activity after 21 days of culture (FIG. 19).

We found that NRVMs cultured in both 3D RTG-CNT and 3D RTG-lysine had more frequent calcium oscillations compared to cells cultured on 2D gelatin controls and that NRVMs cultured in the 3D RTG-CNT system had more homogenous calcium oscillations (synchronized beating with similar frequency) compared with the RTG-lysine system. Moreover, 95% of the total cells analyzed in the RTG-CNT system present this synchronized calcium transients profile, where 83% and 94% of the total cells analyzed in the RTG-lysine system and in the gelatin control group respectively, present a similar calcium transients profile as shown in FIG. 19. Therefore, our findings support the idea that the combination of a 3D culture environment and the presence of CNT may improve CMs intracellular communication and function towards a more mature cardiac phenotype.

Spontaneous beating of NRVMs cultured in the RTG systems and on 2D gelatin controls was also measured by atomic force microscopy (AFM) at day 21. Among other applications, AFM can be used to study the biomechanical properties of cells by measuring the deflection of a flexible cantilever while interacting with the cell surface; previous studies have used AFM to successfully measure the altered nuclear mechanical properties of CMs with the cardiomyopathy LMNA D192G mutation by AFM. In addition to measuring biomechanical properties of cells, AFM can be used to measure the height of spontaneous beating of CMs (FIG. 20). In the illustrated examples, NRVMs were cultured in RTG systems (also referred to herein as compositions) as described herein for 21 days and used the reversible property of the gels to retrieve cells for investigation: reducing the temperature to 25° C., the RTGs became solutions, whereupon CMs migrated to the bottom of the plate, and these were analyzed. The beating activity of NRVMs was registered as peaks in the deflection of the cantilever, giving information about the frequency and height registered during the polarization and depolarization phases. FIG. 21 shows the beating activity of CMs cultured in different conditions. Our results obtained with the AFM were similar to those obtained with the calcium transient analysis; therefore, this corroborates the importance of a 3D niche to provide cell support and intracellular communication. On the other hand, NRVMs that were growing in the 3D RTG-CNT presented higher contraction while beating (FIG. 21), suggesting that the RTG-CNT niche supports a more efficient CMs contraction.

Since our results suggested that NRVMs grown in the 3D RTG-CNT matrix exhibit a more mature electrophysiological phenotype, we were interested in assessing whether this might extend to the expression of genes that are established markers of physiological growth. At the same time, we also wanted to verify whether culturing NRVM in the 3D RTG-CNT polymer might prevent the expression of genes associated with pathologic hyper-trophy upon treatment with phenylephrine. To this purpose, cardiomyocytes were isolated and cultured as previously described. At days 21 after culturing NRVM in the 3D RTG-CNT polymer, the level of expression of five key genes involved in the growth/fetal gene expression program (rat beta-myosin heavy chain ($\beta$MHC), alpha-myosin heavy chain (RMHC), A-type Natriuretic Peptide (ANP), Sarcoplasmic Reticulum Ca2 þ ATPase 2a (SERCA2a) and brain natriuretic peptide (BNP) was quantified by transcript specific real-time PCR amplification (RT-PCR). NRVM growing in 2D gelatin coated culture plates were used as control. The housekeeping gene GAPDH was used to normalize the results. FIG. 22 shows the gene expression of NRVM cultured for 21 days in 2D gelatin coated dishes and in the 3D RTG-CNT scaffold. As illustrated in FIG. 22, the fetal gene expression decreased (ANP and BNP) on the cells growing in the 31) RTG-CNT system, whereas the SERCA and $\alpha$-MHC (gene expressed only in mature cardiomyocytes) highly expressed when compared with the gelatin control. These results demonstrate that the 3D RTG-CNT promotes CMs maturation.

In addition, a pilot in vivo study of the RTG-CNT and the RTG systems was performed in mice to investigate the biocompatibility of the RTG-CNT polymer. RTG polymer and saline injections were used as controls. FIG. 23 shows the solution injections into the heart tissue. FIG. 24 illustrates the echocardiographic results in the three groups assessed: RTG-CNT, RTG and saline solution. Results demonstrate that, both RTG-CNT and RTG scaffolds were well tolerated and biocompatible with the heart tissue without affecting its normal function.

In mammals, CMs proliferation rapidly ceases after birth. Consequently, the ability of the adult heart to repair itself following injury is very restricted. miRNAs have emerged as important modulators of cardiovascular biology, repair, and regeneration. Liposomal encapsulation of miRNA has been shown to facilitate cellular uptake by endocytosis and protecting the constructs from degradation. However, positively charged lipids induce dose-dependent toxicity, limiting the use of this approach in clinics. To overcome this limitation, we assessed the use of the RTG-CNT systems as a delivery system for miRNA transfection. FIG. 25 shows our proof-of-concept experiment NRVM transfected with a fluorescent-labeled miRNA using the RTG-CNT system to demonstrate the feasibility of the assay and stability of the miRNA at 72 h. alpha sarcomeric actinin was used as cardiac marker. Although we have demonstrated that the RTG-CNT polymer promotes CMs proliferation, the addition of miR-NAs could be beneficial to improve cardiac repair.

A pilot miRNA delivery was performed using a RTG-CNT hydrogel, as described herein, in a myocardial infarction (MI) model and in a normal heart. Briefly, in 2-month-old male CD1 mice a left thoracotomy was performed via the fourth intercostal space. The left anterior descending coronary artery was ligated with an 8-0 silk suture near its origin between the pulmonary outflow tract and the edge of the left atrium for 45 minutes turning the anterior wall of the left ventricle (LV) pale. After MI, 30 µl of RTG-CNT solution containing 24 µg of synthetic miR-199a-3p mimics, or 30 was injected into the left ventricle anterior wall using a 0.3 ml insulin syringe with a 30-gauge needle.

For controls, RTG-CNT hydrogel without miRNA and saline were also injected after MI. All anatomical structures were visualized with a stereomicroscope (Leica). After injection, intercostal space, muscles and skin were sutured and mice were extubated to re-establish normal breathing. For additional controls, RTG-CNT with synthetic miR-199a-3p mimics, RTG-CNT without miRNAs and saline were injected in animals without MI. Seven days post injection, mice were sacrificed by cervical dislocation, chest was cut open and cardiac perfusion with PBS was done. Then the injection site was located and the left ventricle free wall of heart was isolated, homogenized and RNA was isolated. Using Quantitative polymerase chain reaction amplification measurements, the levels of transfected miR-199a-3p mimic in left ventricle free wall (injection site) were quantified and normalized to PBS injection (MI and normal respectively). All the samples were normalized using 5S ribosomal RNA (5S rRNA). FIG. 26 illustrate results in which the RTG-CNT hydrogel was able to deliver miR- 199a-3p mimics in either a heart with MI and in a normal heart, evidencing that the RTG-CNT hydrogel can serve as miRNA delivery system.

The results above suggest that the RTG-CNT may be superior to RTG-lysine and the 2D gelatin controls in being supportive of long term cardiac cell survival (up to 21 days), proliferation, maturation and Function. The chemical conjugation of CNT to the RTG-lysine improves the biocompatibility of the system. In addition, the pilot in vivo study indicates that the RTG-CNT is biocompatible and well tolerated by the heart tissue without affecting its function. Moreover, the RTG-CNT can be used a delivery system for miRNA transfection. Our results demonstrate that RTG-CNT polymer has the potential to be used for clinical applications.

CNT can tightly interact with CMs, penetrating the cell membrane. CNT are cylindrically hollow shaped nanostructures, made of one or more concentric rolled-up graphene sheets, which possess high surface area. Since CNT are hollow materials and because we previously observed a tight CNT-CMs interaction, it is possible that CNT may adsorb nutrients from the external media and further act as carriers, helping in a more direct cells protein adsorption. In addition, because CNT are highly electrically conductive materials, several investigations indicate that CNT improve intracellular communication, promoting CMs maturation. The micro-porous architecture of the 3D RTG scaffolds promotes a more organized cellular alignment mimicking the cardiac tissue. Therefore, both 3D RTG niche and CNT enhance CMs survival, proliferation maturation and function.

Safety concerns of CNT are often raised when CNT are used in biological environments. CNT dispersed in polymeric scaffolds can result in variable toxicity effects, since the CNT can be released from the polymeric matrix. Here, however, a safe alternative is offered by chemically conjugating CNT into a non-biodegradable material. We have previously demonstrated that our RTG systems, with the present chemistry used in this investigation, are non-biodegradable under acidic and enzymatic conditions. This particular characteristic may keep the conjugated CNT into the polymeric matrix. In addition, the MWCNT-COOH synthesis procedure described herein may avoid further toxic effect caused by metallic impurities and oxidative debris presented in oxidized CNT-COOH.

As set forth above, the carbon nanotube-functionalized reverse thermal gel polymer and composition as described herein can be used as an injectable conductive culture system, providing both topographical and electrophysiological cues for native CMs. The polymer and composition can promote long-term CMs survival with a more aligned cell organization, as observed by immunocytochemistry, and improved cellular function and maturation, as shown by more robust Ca2+ transients, stronger contractility by AFM and expression of mature CMs genes. In addition, the combination of the 3D niche and the CNT favors CMs proliferation and suppresses long-term fibroblast proliferation. The chemical conjugation of CNT to the RTG-lysine system improves CMs survival, proliferation, alignment and function, proving that the RTG-CNT polymer is non-cytotoxic in vitro. RTG-CNT injection in mice heart tissue, demonstrate that our polymer is well tolerated and biocompatible. In addition, the RTG-CNT can be used as a delivery system for biomolecules, such as miRNAs. Finally, we believe that this low viscosity RTG-CNT system that transitions to a 3D matrix by temperature stimuli not only has a tremendous potential for minimally invasive approaches to repair damaged heart tissue, but also could be potentially used as 3D scaffold for in vitro investigations.

The present invention has been described above with reference to a number of exemplary embodiments and examples. It should be appreciated that the particular embodiments shown and described herein are illustrative of the preferred embodiments of the invention and its best mode, and are not intended to limit the scope of the invention. It will be recognized that changes and modifications may be made to the embodiments described herein without departing from the scope of the present invention. These and other changes or modifications are intended to be included within the scope of the present invention.

We claim:

1. A method of forming a carbon nanotube-functionalized reverse thermal gel composition, the method comprising the steps of:
    synthesizing multi-walled carbon nanotubes with COOH groups;
    synthesizing a reverse thermal gel polymer backbone;
    conjugating poly-L-lysine onto the polymer backbone; and
    conjugating at least one of the carbon nanotubes onto the L-lysine.

2. The method of claim 1, further comprising a step of conjugating another poly-L-lysine onto the at least one of the carbon nanotubes.

3. The method of claim 1, wherein the step of synthesizing a reverse thermal gel polymer backbone comprises reacting N—BOC-serinol, urea, and a diisocyanate to form PSHU.

4. The method of claim 1, wherein the step of synthesizing a reverse thermal gel polymer backbone comprises reacting NIPAAm and a carboxylic acid to form PNIPAAm-COOH.

5. The method of claim 1, wherein the step of synthesizing a reverse thermal gel polymer backbone comprises conjugating PNIPAAm-COOH and PSHU—$NH_2$.

6. The method of claim 1, further comprising a step of forming a dispersion comprising the carbon nanotubes with a COOH group in a solvent.

* * * * *